(12) United States Patent
Rana

(10) Patent No.: US 6,503,713 B1
(45) Date of Patent: Jan. 7, 2003

(54) METHODS FOR IDENTIFYING RNA BINDING COMPOUNDS

(75) Inventor: Tariq M Rana, Piscataway, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/679,451

(22) Filed: Oct. 4, 2000

Related U.S. Application Data

(60) Provisional application No. 60/157,646, filed on Oct. 4, 1999.

(51) Int. Cl.$^7$ .......................... C12Q 1/68; C07H 19/00; C07H 21/00; A01N 43/04

(52) U.S. Cl. ................. 435/6; 435/5; 435/7.1; 435/7.2; 514/44; 530/300; 536/22.1; 536/23.1; 536/24.3

(58) Field of Search .......................... 435/5, 6, 7.1, 7.2; 514/1, 44; 530/300; 536/22.1, 23.1, 24.3

(56) References Cited

U.S. PATENT DOCUMENTS

| | | | |
|---|---|---|---|
| 5,510,240 A | 4/1996 | Lam et al. ................ 435/7.1 |
| 5,593,835 A | * 1/1997 | Rando et al. ............... 435/6 |
| 5,712,096 A | * 1/1998 | Stern et al. ................ 435/6 |
| 5,866,341 A | * 2/1999 | Spinella et al. ........... 435/7.1 |
| 6,004,749 A | 12/1999 | Giordano et al. ........... 435/6 |
| 6,090,912 A | 7/2000 | Lebl et al. ............... 530/300 |
| 6,107,029 A | 8/2000 | Giordano .................. 435/6 |

FOREIGN PATENT DOCUMENTS

WO   WO 97/09342   3/1997

OTHER PUBLICATIONS

Needels et al., 1993, "Generation and screening of an oligonucleotide–encoded synthetic peptide library", Proc. Natl. Acad. Sci. USA 90:10700–10704.
Aboul–ela et al. (1995) The structure of the human immunodeficiency virus type–1 TAR RNA reveals principles of RNA recognition by Tat protein. J. Mol. Biol. 253:313–332.
Bayer (1991) Towards The Chemical Synthesis of Proteins. Angew. Chem. 30:113–129.
Beal & Dervan (1991) Second structural motif for recognition of DNA by oligonucleotide–directed triple–helix formation. Science 1991 251(4999):1360–1363.
Chastain & Tinoco (1991) Structural elements in RNA. Prog Nucleic Acid Res Mol Biol 41:131–177.
Chow & Bogdan (1997) A structural basis for RNA–ligand interactions. Chemical Reviews 97:1489–1514.
Churcher et al. (1993) High affinity binding of TAR RNA by the human immunodeficiency virus type–1 tat protein requires base–pairs in the RNA stem and amino acid residues flanking the basic region, J. Mol. Biol. 230:90–110.

(List continued on next page.)

Primary Examiner—Jezia Riley
(74) Attorney, Agent, or Firm—Pennie & Edmonds LLP

(57) ABSTRACT

The present invention relates to methods of screening for compounds that bind RNA molecules. In particular, the methods of the invention comprise screening a library of test compounds, each of which is attached to a solid support, with a dye-labeled RNA molecule to form a dye-labeled target RNA:support-attached test compound complex. By virtue of the dye label on the target RNA, the support becomes labeled and can be separated from unlabeled solid supports. The present invention further relates to methods of inhibiting an RNA-protein interaction, to methods of screening for compounds that increase or decrease the production of a protein, and to methods of screening for a compound that is capable of treating or preventing a disease whose progression is associated with an in vivo binding of a test compound to a target RNA.

50 Claims, 4 Drawing Sheets

OTHER PUBLICATIONS

Cordingley et al. (1990) Sequence–Specific Interaction of Tat Protein and Tat Peptides with the Transactivation–Responsive Sequence Element of Human Immunodeficiency Virus Type 1 in vitro. Proc. Natl. Acad. Sci. USA 87:8985–8989.

Felber & Pavlakis (1988) A quantitative bioassay for HIV–1 based on trans–activation. Science 239:184–187.

Frankel A. D. & Pabo (1988) Cellular uptake of the tat protein from human immunodeficiency virus. Cell 55:1189–1194.

Gottesfeld et al. (1997) Regulation of gene expression by small molecules. Nature 387(6629):202–205.

Hamy et al. (1998) A new class of HIV–1 Tat antagonist acting through Tat–TAR inhibition. Biochemistry 37(15):5086–5095.

Hamy et al. (1997) An inhibitor of the Tat/TAR RNA interaction that effectively suppresses HIV–1 replication. Proc. Natl. Acad. Sci. USA 94:3548–3553.

Helene et al. (1992) Control of gene expression by triple helix–forming oligonucleotides. The antigene strategy. Ann N Y Acad Sci 660:27–36.

Ho et al., (1994) Specific inhibition of formation of transcription complexes by a calicheamicin oligosaccharide: a paradigm for the development of transcriptional antagonists. Proc Natl Acad Sci U S A 91(20):9203–9207.

Huq et al. (1999) Controlling human immunodeficiency virus type 1 gene expression by unnatural peptides. Biochemistry 38:5172–5177.

Hwang et al. (1999) Inhibition of gene expression in human cells through small molecule–RNA interactions. Proc. Natl. Acad. Sci. USA 96(23):12977–13002.

Jakobovits et al. (1988) A discrete element 3' of human immunodeficiency virus 1 (HIV–1) and HIV–2 mRNA initiation sites mediates transcriptional activation by an HIV trans activator. Mol. Cell. Biol. 8:2555–2561.

Jones & Peterlin (1994) Control of RNA initiation and elongation at the HIV–1 promoter. Annu Rev Biochem 63:717–743.

Liu et al. (1996) Sequence–selective carbohydrate–DNA interaction: Dimeric and monomeric forms of the calicheamicin oligosaccharide interfere with transcription factor function. Proc Natl Acad Sci U S A 93(2):940–944.

Maher et al. (1991) Oligonucleotide–directed DNA triple –helix formation: an approach to artificial repressors? Antisense Res Dev 1(3):277–281.

Mei et al. (1998) Inhibitors of protein–RNA complexation that target the RNA: specific recognition of human immunodeficiency virus type 1 TAR RNA by small organic molecules. Biochemistry 37(40):14204–14212.

Mei et al. (1997) Discovery of selective, small–molecule inhibitors of RNA complexes—I. The Tat protein/TAR RNA complexes required for HIV–1 transcription. Bioorg. Med. Chem. 5:1173–1184.

Miller (1996) Development of antisense and antigene oligonucleotide analogs. Prog Nucleic Acid Res Mol Biol 1996;52:261–291.

Milligan et al. (1987) Oligoribonucleotide synthesis using T7 RNA polymerase and synthetic DNA templates. Nucleic Acids Res. 15:8783–8798.

Misiura et al. (1990) Biotinyl and phosphotyrosinyl phosphoramidite derivatives useful in the incorporation of multiple reporter groups on synthetic oligonucleotides. Nucleic Acids Res. 18:4345–4354.

Muller et al. (1991) Interaction of fluorescently labeled dideoxyncleotides with HIV–1 reverse transcriptase. Biochemistry 30:3709–3715.

Neenhold & Rana (1995) Major groove opening at the HIV–1 Tat binding site of TAR RNA evidenced by a rhodium probe. Biochemistry 34:6303–6309.

Nielsen (1999) Applications of peptide nucleic acids. Curr Opin Biotechnol 10(1):71–75.

Nordeen (1988) Luciferase reporter gene vectors for analysis of promoters and enhancers. Bio Techniques 6:454–457.

Ohlmeyer et al. (1993) Complex synthetic chemical libraries indexed with molecular tags. Proc Natl Acad Sci U S A 90(23):10922–10926.

Ping et al. (1997) Dynamics of RNA–protein interactions in the HIV–1 Rev–RRE complex visualized by 6–thioguanosine–mediated photocrosslinking. RNA 3:850–860.

Puglisi et al. (1992) Conformation of the TAR RNA–arginine complex by NMR spectroscopy. Science 257:76–80.

Scaringe et al. (1990) Chemical synthesis of biologically active oligoribonucleotides using beta–cyanoethyl protected ribonucleoside phosphoramidites. Nucleic Acids Res. 18:5433–5441.

Shah et al. (1994) Synthesis of uridine phosphoramidite analogs: reagents for site–specific incorporation of photoreactive sites into RNA sequences. Bioconjugate Chem. 5:508–512.

Shah et al. (1996) Incorporation of an artificial protease and nuclease at the HIV–1 Tat binding site of trans–activation responsive RNA. Bioconjugate Chem. 7:283–289.

Still (1996) Discovery of sequence–selective peptide binding by synthetic receptors using encoded combinatorial libraries. Accounts of Chemical Research 29:(3) 155–163.

Wang & Rana (1996) RNA conformation in the Tat–TAR complex determined by site–specific photo–cross–linking. Biochemistry 35:6491–6499.

Weeks & Crothers (1993) Major groove accessibility of RNA. 261(5128):1574–1577.

White et al. (1998) Recognition of the four Watson–Crick base pairs in the DNA minor groove by synthetic ligands. Nature 391(6666):468–471.

\* cited by examiner

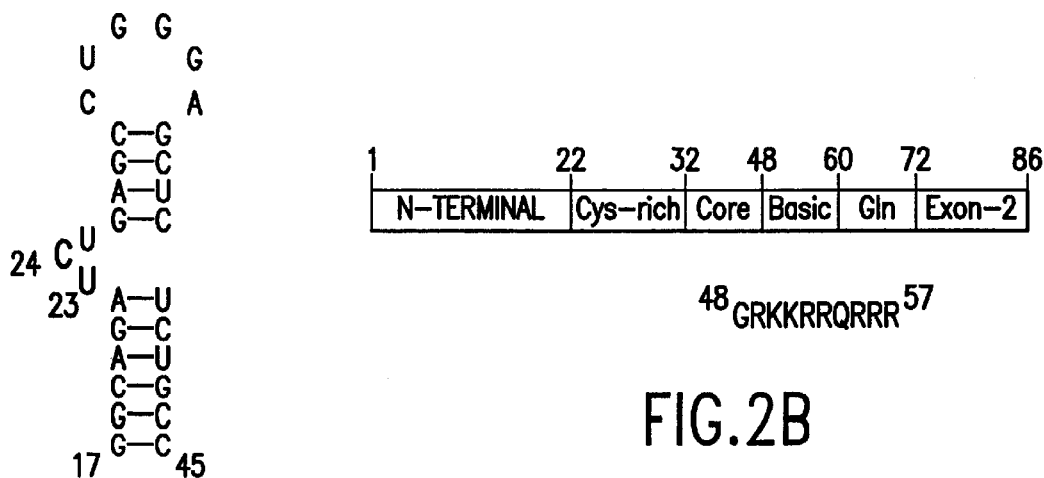
FIG.2A
FIG.2B
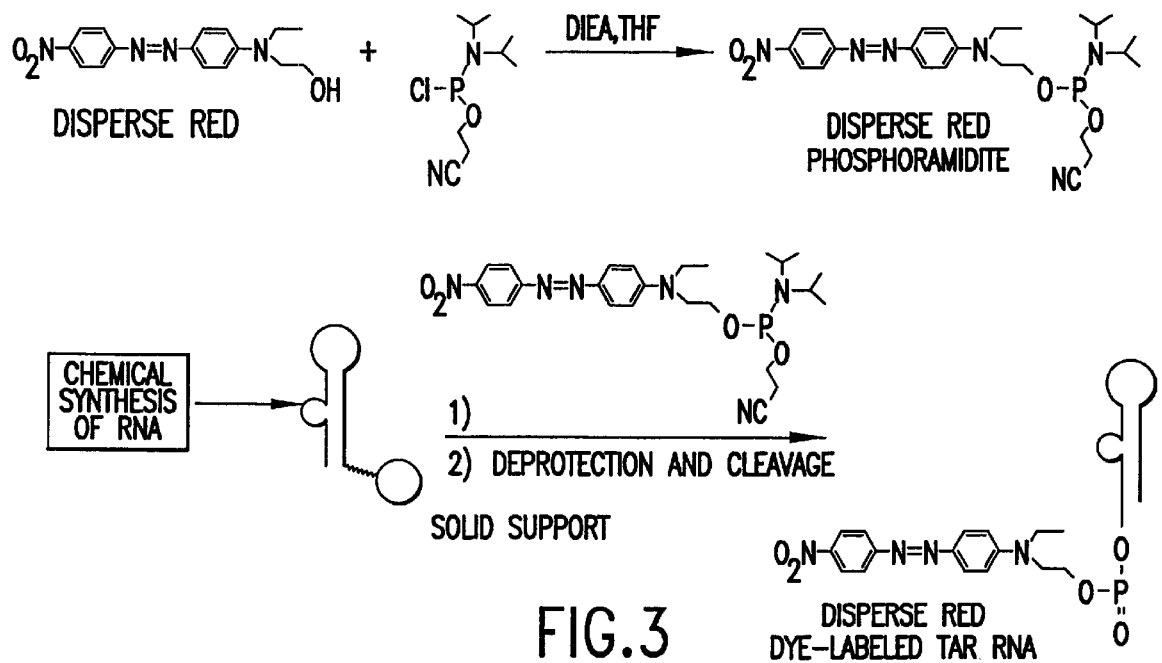
FIG.3

1

METHODS FOR IDENTIFYING RNA BINDING COMPOUNDS

This application claims the benefit of U.S. Provisional Application No. 60/157,646, filed Oct. 4, 1999, which is incorporated herein by reference in its entirety.

This invention was made with government support under grant nos. AI41404 and AI01369 awarded by the National Institute of Health. The government has certain rights in the invention.

1. FIELD OF THE INVENTION

The present invention relates to methods for identifying compounds that bind RNAs. In particular, the present invention relates to methods for using a target RNA having a detectable label to screen a library of test compounds immobilized on one or more solid supports, and preferably, on one or more individual beads. Contacting a target RNA to a test compound can form a dye-labeled target RNA:support-attached test compound complex. Dye-labeled target RNA molecules in the complex label the test compounds attached to the solid supports, which can be separated from a plurality of unlabeled solid supports. Finally, the structure of the test compound attached to the solid support can be determined by decoding the solid support.

2. BACKGROUND OF THE INVENTION

Protein-nucleic acid interactions are involved in many cellular functions, including transcription, RNA splicing, and translation. Readily accessible synthetic molecules that can bind with high affinity to specific sequences of single- or double-stranded nucleic acids have the potential to interfere with these interactions in a controllable way, making them attractive tools for molecular biology and medicine. Successful approaches for blocking binding sites on target nucleic acids include using duplex-forming antisense oligonucleotides (Miller, P. S. (1996) *Progress in Nucl. Acid Res. & Mol. Biol.* 52, 261–291) and peptide nucleic acids ("PNA") (Nielsen, P. E. (1999) *Current Opinion in Biotechnology* 10, 71–75), which bind to nucleic acids via Watson-Crick base-pairing and using triplex-forming anti-gene oligonucleotides (Ping, Y.-H. et al. (1997) *RNA* 3, 850–860) and pyrrole-imidazole polyamide oligomers (Gottesfeld, J. M. et al. (1997) *Nature* 387, 202–205; White, S. et al. (1998) *Nature* 391, 468–471), which are specific for the major and minor grooves of a double helix, respectively. One advantage of using oligonucleotide-based classes of nucleic acid binding compounds is that they are easily identified by their primary or secondary structures. Another approach employs carbohydrate-based ligands, calicheamicin oligosaccharides, which interfere with the sequence-specific binding of transcription factors to DNA and inhibit transcription in vivo (Ho, S. N. et al. (1994) *Proc. Natl. A cad. Sci. USA* 91, 9203–9207; Liu, C. et al. (1996) *Proc. Natl. Acad. Sci. USA* 93, 940–944).

Nucleic acids, and in particular RNA, may fold into complex tertiary structures consisting of local motifs such as loops, bulges, pseudoknots and turns (Chastain, M. & Tinoco, I., Jr. (19991) *Progress in Nucleic Acid Res. & Mol. Biol.* 41, 131–177; Chow, C. S. & Bogdan, F. M. (1997) *Chemical Reviews* 97, 1489–1514), which are critical for protein-RNA interactions (Weeks, K. M. & Crothers, D. M. (1993) *Science* 261, 1574–1577). The dependence of these interactions on the native three-dimensional structure of RNA makes it difficult to design synthetic agents using general, simple-to-use recognition rules analogous to those for the formation of double- and triple-helical nucleic acids. Since RNA-RNA and protein-RNA interactions may be important in, e.g., viral and microbial disease progression, it would be advantageous to have a general method for rapidly identifying compounds that bind to specific RNAs and that may prove to be antagonists of in vivo protein-RNA or RNA-RNA interactions.

Currently available methods for screening combinatorial compound libraries for compounds that bind to RNA are labor intensive and are not well-adapted to high throughput screening. Moreover, if a mixture of compounds is tested, using time-consuming deconvolution strategies may be necessary to identify the individual compounds in the mixture that have the most desirable properties (Hamy et al. (1997) *Proc. Natl. Acad. Sci. USA* 94, 3548–3553; Hamy et al. (1998) *Biochemistry* 37, 5086–5095). One frequently used method of identifying compounds that disrupt protein-RNA interactions is the gel mobility shift assay (Mei et al. (1998) *Biochemistry* 37, 14204–14212; Mei et al. (1997) *Bioorganic & Medicinal Chem.* 5:1173–84; Hamy et al. (1997) *Proc. Nat. Acad. Sci. USA* 94, 3548–3553; Hamy et al. (1998) *Biochemistry* 37, 5086–5095). In this assay, a protein/labeled RNA complex is formed, various concentrations of a potential inhibitor are added, and the resulting dissociation of the complex is monitored by observing the changing mobility of the labeled RNA on a gel. Although a dissociation constant for the potential inhibitor can be calculated using the assay, testing many compounds in this way is time consuming. Furthermore, additional experiments, such as RNase footprinting or NMR, may have to be performed to ensure that disruption of the complex is due to the compound binding to the RNA rather than to the protein (Hamy et al. (1997) *Proc. Natl. Acad. Sci. USA* 94, 3548–3553; Hamy et al. (1998) *Biochemistry* 37:5086–5095). Other methods for testing compounds for specific RNA binding include electrospray ionization mass spectrometry (ESI-MS), filter binding assays, and scintillation proximity assays (SPA) (Mei et al. (1998) *Biochemistry* 37, 14204–14212; Mei et al. (1997) *Bioorganic & Medicinal Chem.* 5:1173–84). Yet another method for screening for RNA binding compounds involves detecting changes in RNA conformation upon binding of the compound by, e.g., hybridization, treatment with conformation-specific nucleases, binding to matrices specific for single- or double-stranded nucleic acids or fluorescence resonance energy transfer (International Patent Publication WO 97/09342, published Mar. 13, 1997). The method described in WO 97/09342 has limited usefulness because not all compounds that bind to RNA will cause a detectable conformational change in the nucleic acid.

Screening of combinatorial libraries may also be performed using a computer. For example, databases of RNA three-dimensional structures can be examined to identify common "molecular-interaction sites," i.e., general structural motifs through which RNAs interact with other molecules, such as proteins. These molecular-interaction sites can then be used to computationally design compounds that bind at these sites. Virtual library compounds can be screened on the basis of their conformation, binding affinity, strain energy, solubility, and the like (Li (1998) DDT 3:105; Walters (1998) DDT 3:160). Once library compounds are selected, the compounds can be synthesized and tested. Although these methods are well-adapted to high-throughput screening of compounds, they are dependent on the accuracy of the RNA structures in the databases and on the ability of computer programs to accurately predict the conformations of potential inhibitors in solution.

Accordingly, there is clearly a need for fast and efficient methods for screening combinatorial compound libraries for molecules that bind to RNAs and potentially disrupt protein-RNA or RNA-RNA interactions.

Citation or identification of any reference in Section 2 of this application is not an admission that such reference is available as prior art to the present invention.

3. SUMMARY OF THE INVENTION

In a first embodiment, the present invention relates to a method for identifying a test compound that binds to a target RNA molecule, comprising the steps of: (a) contacting a dye-labeled target RNA molecule with substantially one type of test compound attached to a solid support, thereby providing a dye-labeled target RNA:support-attached test compound complex; and (b) determining the structure of the substantially one type of test compound of the RNA:test compound complex.

In a second embodiment, the present invention relates to a method for identifying a test compound that binds to a target RNA molecule, comprising the step of determining the structure of substantially one type of test compound of an RNA:test compound complex formed from contacting a dye-labeled target RNA molecule with substantially one type of test compound attached to a solid support.

In a third embodiment, the present invention relates to a method for forming a target RNA:test compound complex, comprising the step of contacting a target RNA molecule with the test compound identified from a method comprising the steps of: (a) contacting a dye-labeled target RNA molecule with substantially one type of test compound attached to a solid support, thereby providing a dye-labeled target RNA:support-attached test compound complex; and (b) determining the structure of the substantially one type of test compound of the RNA:test compound complex.

In a fourth embodiment, the present invention relates to a method for increasing or decreasing the production of a protein comprising the step of contacting a target messenger RNA molecule that encodes said protein with the test compound identified from a method comprising the steps of: (a) contacting a dye-labeled target RNA molecule with substantially one type of test compound attached to a solid support, thereby providing a dye-labeled target RNA:support-attached test compound complex; and (b) determining the structure of the substantially one type of test compound of the RNA:test compound complex.

In a fifth embodiment, the present invention relates to a method for treating or preventing a disease whose progression is associated with in vivo binding of a test compound to a target RNA, comprising administering to a patient in need of such treatment or prevention a therapeutically effective amount of the test compound, or a pharmaceutically acceptable salt thereof, identified according to a method comprising the steps of: (a) contacting a dye-labeled target RNA molecule with substantially one type of test compound attached to a solid support, thereby providing a dye-labeled target RNA:support-attached test compound complex; and (b) determining the structure of the substantially one type of test compound of the RNA:test compound complex.

In a sixth embodiment, the present invention relates to a method for treating or preventing HIV infection or AIDS in a patient, comprising administering to a patient in need of such treatment or prevention a therapeutically effective amount of a compound selected from the group consisting of:

$H_2N$-(L)Lys-(D)Lys-(L)Asn-OH,
$H_2N$-(L)Lys-(D)Lys-(D)Asn-OH,
$H_2N$-(L)Lys-(L)Lys-(L)Asn-OH,
$H_2N$-(L)Arg-(D)Lys-(L)Asn-OH,
$H_2N$-(L)Arg-(D)Lys-(L)Val-OH,
$H_2N$-(L)Arg-(D)Lys-(L)Arg-OH,
$H_2N$-(D)Thr-(D)Lys-(L)Asn-OH, and
$H_2N$-(D)Thr-(D)Lys-(L)Phe-OH

4. BRIEF DESCRIPTION OF THE FIGURES

FIG. 1 shows a schematic representation of using the present methods to identify the chemical structure of a test compound that binds to TAR RNA.

FIG. 2A shows the sequence and secondary structure of the minimal sequence of TAR RNA (SEQ. ID. NO. 1), including residues in the bulge region that interact with Tat protein, required for Tat responsiveness in vivo; FIG. 2B shows the regions of the HIV-1 Tat protein and the sequence of the Tat (48–57) peptide (SEQ. ID. NO. 2) that binds TAR RNA with high affinity.

FIG. 3 shows a synthesis of disperse red-labeled TAR RNA using phosphoramidite chemistry.

5. DETAILED DESCRIPTION OF THE INVENTION

Figure 1:
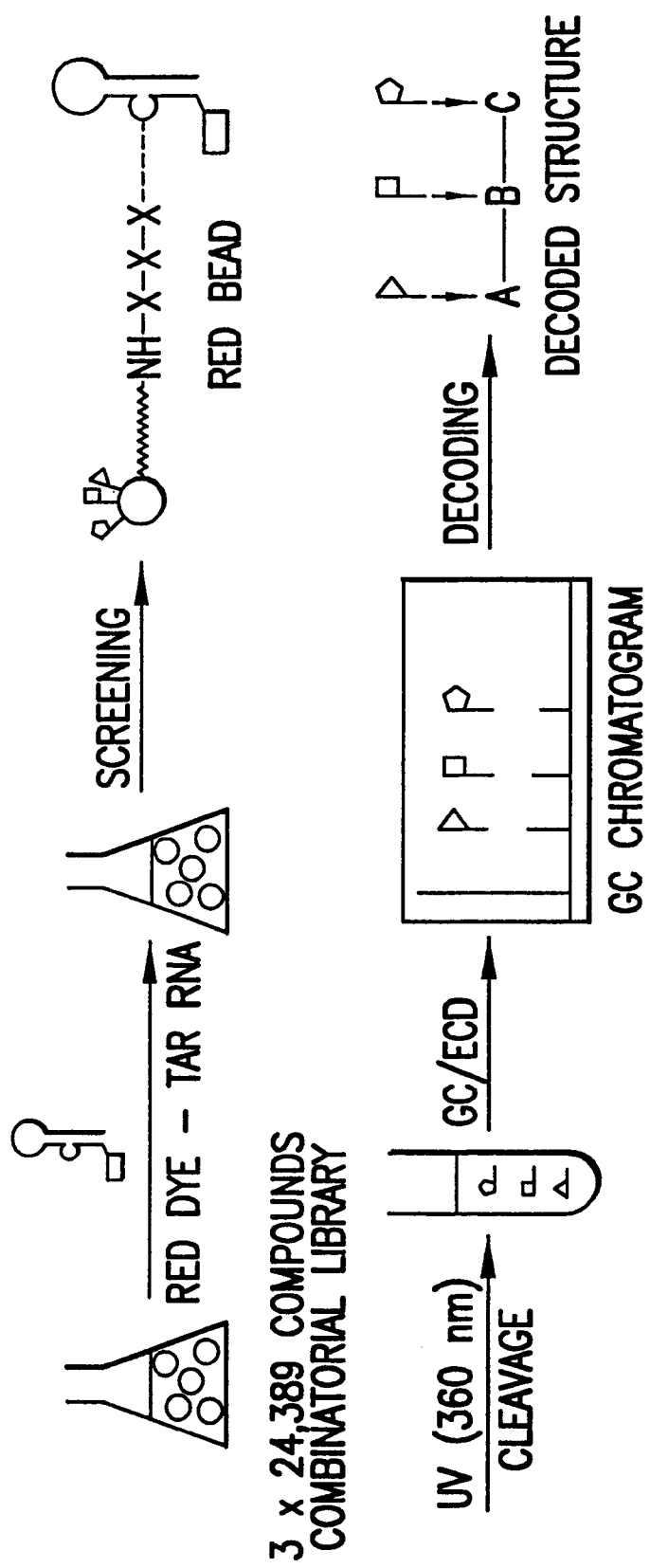

The present invention relates to a method for identifying a test compound that binds to RNA using a library of test compounds attached to a solid support. In particular, a plurality of test compounds is attached to a plurality of solid supports, e.g. polymer beads, with each solid support having substantially one type of test compound attached to its surface. The plurality of solid supports of the library is exposed in aqueous solution to RNA having a detectable label, forming a dye-labeled target RNA:support-attached test compound complex. Binding of target RNA molecules to a particular test compound labels the solid support, e.g., bead, comprising that compound, which can then be physically separated from other, unlabeled solid supports. Once labeled solid supports are identified, the chemical structures of the test compounds thereon can be determined, e.g., by reading a code on the solid support that correlates with the structure of the attached test compound. Thus, the methods of the present invention provide a simple, sensitive assay for high-throughput screening of entire test compound libraries, where test compounds in a library that bind an RNA of interest are easily separated from non-RNA-binding compounds, and where the structures RNA-binding and, accordingly, active test compounds are easily determined by encoding methods.

As used herein, a "library" refers to a plurality of test compounds with which a target RNA molecule is contacted. A library can be a combinatorial library, e.g., a collection of test compounds synthesized using combinatorial chemistry techniques.

As used herein, a "dye" refers to a molecule that, when exposed to radiation, emits radiation at a level that is detectable visually or via conventional spectroscopic means. As used herein, a "visible dye" refers to a molecule having a chromophore that absorbs radiation in the visible region of the spectrum (i.e., having a wavelength of between about 400 nm and about 700 mn) such that the transmitted radiation is in the visible region and can be detected either visually or by conventional spectroscopic means. As used herein, an "ultraviolet dye" refers to a molecule having a chromophore that absorbs radiation in the ultraviolet region of the spectrum (i.e., having a wavelength of between about 30 nm and about 400 nm). As used herein, an "infrared dye" refers to a molecule having a chromophore that absorbs radiation in the infrared region of the spectrum (i.e., having a wavelength between about 700 mn and about 3,000 nm). A "chromophore" is the network of atoms of the dye that, when exposed to radiation, emits radiation at a level that is detectable visually or via conventional spectroscopic means. One of skill in the art will readily appreciate that although a dye absorbs radiation in one region of the spectrum, it may emit radiation in another region of the spectrum. For example, an ultraviolet dye may emit radiation in the visible region of the spectrum. One of skill in the art will also readily appreciate that a dye can transmit radiation or can emit radiation via fluorescence or phosphorescence.

The phrase "pharmaceutically acceptable salt(s)," as used herein includes but is not limited to salts of acidic or basic groups that may be present in test compounds identified using the methods of the present invention. Test compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Test compounds that include an amino moiety may form pharmaceutically or cosmetically acceptable salts with various amino acids, in addition to the acids mentioned above. Test compounds that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

By "substantially one type of test compound," as used herein, is meant that at least about 96% of all test compounds per support are of the same type.

Section 5.1 describes examples of protein-RNA interactions that are important in a variety of cellular functions. Compounds that inhibit these interactions by binding to the RNA and successfully competing with the natural protein or RNA ligand of the RNA may be important, e.g., in treating or preventing a dissease or abnormal condition, such as an infection or unchecked growth. Section 5.2 describes the use of test compounds identified by the methods of the invention for treating or preventing a disease or abnormal condition in mammals. Section 5.3 describes RNA-dye conjugates that are useful in the methods of the invention. Section 5.4 describes libraries of test compounds and methods for encoding the library to easily determine the structures of the test compounds of the library. Section 5.5 provides conditions for binding a labeled target RNA to a test compound of a library and detecting RNA binding to a test compound using the methods of the invention.

5.1 Biologycally Important RNA-Ligand Interactions

Nucleic acids, and in particular RNAs, are capable of folding into complex tertiary structures that include bulges, loops, triple helices and pseudoknots, which can provide binding sites for in vivo ligands, such as proteins and other RNAs. RNA-protein and RNA-RNA interactions are important in a variety cellular functions, including transcription, RNA splicing, RNA stability and translation. As used herein, "ligand" refers to a molecule, e.g., a protein or RNA molecule, that binds to a defined binding site on the target RNA.

The methods of the present invention are useful for identifying test compounds that bind to RNA in a high throughput screening assay of libraries of test compounds attached to solid supports. In particular, the methods of the present invention are useful for identifying a test compound that binds to a target RNA at a ligand binding site and inhibits the interaction of that RNA with one or more in vivo ligands. The molecules identified using the methods of the invention are useful for inhibiting the formation of a specific RNA-ligand complex in vivo.

In some embodiments, test compounds identified by the methods of the invention are useful for increasing or decreasing the translation of messenger RNAs ("mRNAs"), e.g., protein production, by binding to one or more regulatory elements in the 5' untranslated region, the 3' untranslated region, or the coding region of the mRNA. Compounds that bind to mRNA can, inter alia, increase or decrease the rate of mRNA processing, alter its transport through the cell, prevent or enhance binding of the mRNA to ribosomes, suppressor proteins or enhancer proteins, or alter mRNA stability. Accordingly, compounds that increase or decrease mRNA translation can be used to treat or prevent disease. For example, diseases associated with protein overproduction, such as amyloidosis, or with the production of mutant proteins, such as cystic fibrosis, can be treated or prevented by decreasing translation of the mRNA that codes for the overproduced protein, thus inhibiting production of the protein. Conversely, the symptoms of diseases associated with decreased protein function, such as hemophelia, may be treated by increasing translation of mRNA coding for the protein whose function is decreased, e.g., factor IX in some forms of hemophilia.

The methods of the invention can be used to identify compounds that bind to mRNAs coding for a variety of proteins with which the progression of diseases in mammals is associated. These mRNAs include, but are not limited to, those coding for amyloid protein and amyloid precursor protein; anti-angiogenic proteins such as angiostatin, endostatin, METH-1 and METH-2; clotting factors such as Factor IX, Factor VIII, and others in the clotting cascade; collagens; cyclins and cyclin inhibitors, such as cyclin dependent kinases, cyclin D1, cyclin E, WAF1, cdk4 inhibitor, and MTS1; cystic fibrosis transmembrane conductance regulator gene (CFTR); cytokines such as IL-1, IL-2, IL-3, IL-4, IL-5, IL-6, IL-7, IL-8, IL-9, IL-10, IL-11, IL-12, IL-13, IL-14, IL-15, IL-16, IL-17 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2, KGF, myotrophin, NGF, OSM, PDGF, somatotrophin, TGF-β, TGF-α and VEGF; antiviral cytokines such as interferons, antiviral proteins induced by interferons, TNF-α, and TNF-β; enzymes such as cathepsin K, cytochrome p-450 and other cytochromes, farnesyl transferase, glutathione-s transferases, heparanase, HMG CoA synthetase, n-acetyltransferase, phenylalanine hydroxylase, phosphodiesterase, ras carboxyl-terminal protease, telomerase and TNF converting enzyme; glycoproteins such as cadherins, e.g., N-cadherin and E-cadherin; cell adhesion molecules; selectins; transmembrane glycoproteins such as CD40; heat shock proteins; hormones such as 5-α reductase, atrial natriuretic factor, calcitonin, corticotrophin releasing factor, diuretic hormones, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, and thyroid stimulating hormone; proteins involved in immune responses, including antibodies, CTLA4, hemagglutinin, MHC proteins, VLA-4, and kallikrein-kininogen-kinin system; ligands such as CD4; oncogene products such as sis, hst, protein tyrosine kinase receptors, ras, abl, mos, myc, fos, jun, H-ras, ki-ras, c-fms, bcl-2, L-myc, c-myc, gip, gsp, and HER-2; receptors such as bombesin receptor, estrogen receptor, GABA receptors, growth factor receptors including EGFR, PDGFR, FGFR, and NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb.

The methods of the invention can be used to identify mRNA-binding test compounds for increasing or decreasing the production of a protein, thus treating or preventing a disease associated with decreasing or increasing the production of said protein, respectively. The methods of the invention may be useful for identifying test compounds for treating or preventing a disease in mammals, including cats, dogs, swine, horses, goats, sheep, cattle, primates and humans. Such diseases include, but are not limited to, amyloidosis, hemophilia, Alzheimer's disease, atherosclerosis, cancer, giantism, dwarfism, hypothyroidism, hyperthyroidism, inflammation, cystic fibrosis, autoimmune disorders, diabetes, aging, obesity, neurodegenerative disorders, and Parkinson's disease.

In other embodiments, test compounds identified by the methods of the invention are useful for preventing the interaction of an RNA, such as a transfer RNA ("tRNA"), an enzymatic RNA or a ribosomal RNA ("rRNA"), with a protein or with another RNA, thus preventing, e.g., assembly of an in vivo protein-RNA or RNA-RNA complex that is essential for the viability of a cell. The term "enzymatic RNA," as used herein, refers to RNA molecules that are either self-splicing, or that form an enzyme by virtue of their association with one or more proteins, e.g., as in RNAse P, telomerase or small nuclear ribonuclear protein particles. For example, inhibition of an interaction between rRNA and one or more ribosomal proteins may inhibit the assembly of ribosomes, rendering a cell incapable of synthesizing proteins. In addition, inhibition of the interaction of precursor rRNA with ribonucleases or ribonucleoprotein complexes (such as RNAse P) that process the precursor rRNA prevent maturation of the rRNA and its assembly into ribosomes. Similarly, a tRNA:tRNA synthetase complex may be inhibited by test compounds identified by the methods of the invention such that tRNA molecules do not become charged with amino acids. Such interactions include, but are not limited to, rRNA interactions with ribosomal proteins, tRNA interactions with tRNA synthetase, RNase P protein interactions with RNase P RNA, and telomerase protein interactions with telomerase RNA.

In other embodiments, test compounds identified by the methods of the invention are useful for treating or preventing a viral, bacterial, protozoal or fungal infection. For example, transcriptional upregulation of the genes of human immunodeficiency virus type 1 ("HIV-1") requires binding of the HIV Tat protein to the HIV trans-activation response region RNA ("TAR RNA"). HWV TAR RNA is a 59-base stem-loop structure located at the 5'-end of all nascent HIV-1 transcripts (Jones, K. A. & Peterlin, B. M. (1994) *Annu. Rev. Biochem.* 63, 717–43). Tat protein is known to interact with uracil 23 in the bulge region of the stem of TAR RNA (FIG. 2(*a*)) (SEQ. ID. NO. 1). Thus, TAR RNA is a potential binding target for test compounds, such as small peptides and peptide analogs, that bind to the bulge region of TAR RNA and inhibit formation of a Tat-TAR RNA complex involved in HIV-1 upregulation. Accordingly, test compounds that bind to TAR RNA are useful as anti-HIV therapeutics (Hamy et al. (1997) *Proc. Natl. Acad. Sci. USA* 94, 3548–3553; Hamy et al. (1998) *Biochemistry* 37, 5086–5095; Mei, H.-Y. et al. (1998) *Biochemistry* 37, 14204–14212), and therefore, are useful for treating or preventing AIDS. Moreover, since the amino acid sequence of the region of Tat protein that binds to TAR RNA with high affinity is well known (FIG. 2(*b*)) (SEQ. ID. NO. 2), a library of test compounds that are chemically and/or structurally similar to a TAR RNA-binding region of Tat can be designed as potential inhibitors of Tat-TAR RNA complex formation (Hwang et al. (1999) *Proc. Natl. Acad. Sci. USA* 96(23):12, 977–13,002).

The methods of the invention can be used to identify test compounds to treat or prevent viral, bacterial, protozoal or fungal infections in a patient. In some embodiments, the methods of the invention are useful for identifying compounds that decrease translation of microbial genes by interacting with mRNA, as described above, or for identifying compounds that inhibit the interactions of microbial RNAs with proteins or other ligands that are essential for viability of the virus or microbe. Examples of microbial target RNAs useful in the present invention for identifying antiviral, antibacterial, antiprotozoal and antifungal compounds include, but are not limited to, general antiviral and anti-inflammatory targets such as mRNAs of INF α, INF γ, RNAse L, RNAse L inhibitor protein, PKR, tumor necrosis factor, interleukins 1–15, and IMP dehydrogenase; internal ribosome entry sites; HIV-1 CT rich domain and RNAse H mRNA; HCV internal ribosome entry site, which is required to direct translation of HCV mRNA; rotavirus NSP3 binding site, which binds the protein NSP3 that is required for rotavirus mRNA translation; HBV epsilon domain; Dengue virus 5' and 3' untranslated regions, including IRES, INF α, INF β and INF γ; plasmodium falciparum mRNAs; the 16S ribosomal subunit ribosomal RNA and the RNA component of RNAse P of bacteria; and the RNA component of telomerase in fungi and cancer cells.

One of skill in the art will appreciate that, although such target RNAs are functionally conserved in various species (e.g., from yeast to humans), they exhibit nucleotide sequence and structural diversity. Therefore, inhibition of, for example, yeast telomerase by an anti-fungal compound identified by the methods of the invention might not interfere with human telomerase and normal human cell proliferation.

Thus, the methods of the invention can be used to identify test compounds that interfere with one or more target RNA-ligand interactions that are essential in the life cycle of a virus, a bacteria, a protozoa or a fungus. Such test compounds can be administered to a patient in need thereof in order to treat or prevent a disease caused by viral, bacterial, protozoal or fungal infections. Such diseases include, but are not limited to, HIV infection, AIDS, human T-cell leukemia, SIV infection, FIV infection, feline leukemia, hepatitis A, hepatitis B, hepatitis C, Dengue fever, malaria, rotavirus infection, severe acute gastroenteritis, diarrhea, encephalitis, hemorrhagic fever, syphilis, legionella, whooping cough, gonorrhea, sepsis, influenza, pneumonia, tinea infection, candida infection, and meningitis.

5.2 Use of Test Compunds Identified Using the Methods of the Invention for Treating or Preventing Diseases In Mammals A test compound identified using the methods of the invention or a pharmaceutically acceptable salt thereof is administered to a patient, preferably a mammal, more preferably a human, suffering from a disease whose progression is associated with a target RNA-ligand interaction in vivo. A test compound is preferably detached from the solid support when it is administered to a patient for treating or preventing a disease. In one embodiment, "treatment" or "treating" refers to an amelioration of a disease, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease, either physically, e.g., stabilization of a discernible symptom, physiologically, e.g., stabilization of a physical parameter, or both. In yet another embodiment, "treatment" or "treating" refers to delaying the onset of a disease.

In certain embodiments, a test compound or a pharmaceutically acceptable salt thereof is administered to a patient, preferably a mammal, more preferably a human, as a preventative measure against a disease associated with an RNA-ligand interaction in vivo. As used herein, "prevention" or "preventing" refers to a reduction of the risk of acquiring a disease. In one embodiment, a test compound or a pharmaceutically acceptable salt thereof is administered as a preventative measure to a patient. According to this embodiment, the patient can have a genetic predisposition to a disease, such as a family history of the disease, or a non-genetic predisposition to the disease. Accordingly, the test compound and pharmaceutically acceptable salts thereof can be used for the treatment of one manifestation of a disease and prevention of another.

When administered to a patient, a test compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a test compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a test compound or a pharmaceutically acceptable salt thereof into the bloodstream.

In specific embodiments, it may be desirable to administer a test compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a test compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a test compound and pharmaceutically acceptable salts thereof can be formulated as a suppository, with traditional binders and vehicles such as triglycerides.

In another embodiment, a test compound and pharmaceutically acceptable salts thereof can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, a test compound and pharmaceutically acceptable salts thereof can be delivered in a controlled release system (see, e.g., Goodson, in Medical Applications of Controlled Release, supra, vol. 2, pp. 115–138 (1984)). Other controlled-release systems discussed in the review by Langer, 1990, *Science* 249:1527–1533) may be used. In one embodiment, a pump may be used (see Langer, supra; Sefton, 1987, CRC *Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science*

228:190; During et al., 1989, *Ann. Neurol.* 25:351; Howard et al., 1989, *J. Neurosurg.* 71:105). In yet another embodiment, a controlled-release system can be placed in proximity of a target RNA of a test compound or a pharmaceutically acceptable salt thereof, thus requiring only a fraction of the systemic dose.

Compositions comprising a test compound or a pharmaceutically acceptable salt thereof ("test compound compositions") can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Test compound compositions, if desired, can also contain minor amounts of wetting or emulsifying agents, or pH buffering agents.

Test compound compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in *Remington's Pharmaceutical Sciences*, Alfonso R. Gennaro ed., Mack Publishing Co. Easton, Pa, 19th ed., 1995, pp. 1447 to 1676, incorporated herein by reference.

In a preferred embodiment, a test compound or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, a test compound or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where a test compound or a pharmaceutically acceptable salt thereof is to be administered by infusion, it can be dispensed, for example, with an infusion bottle containing sterile pharmaceutical grade water or saline. Where the test compound or a pharmaceutically acceptable salt thereof is administered by injection, an ampoule of sterile water for injection or saline can be provided so that the ingredients may be mixed prior to administration.

The amount of a test compound or a pharmaceutically acceptable salt thereof that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 200 milligrams of a test compound or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one test compound is administered, or if a test compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

A test compound and pharmaceutically acceptable salts thereof are preferably assayed in vitro and in vivo, for the desired therapeutic or prophylactic activity, prior to use in humans. For example, in vitro assays can be used to determine whether it is preferable to administer a test compound, a pharmaceutically acceptable salt thereof, and/or another therapeutic agent. Animal model systems can be used to demonstrate safety and efficacy.

A variety of test compounds can be used for treating or preventing diseases in mammals. Types of test compounds include, but are not limited to, peptides, peptide analogs including peptides comprising non-natural amino acids, e.g., D-amino acids (see Table 1, below), phosphorous analogs of amino acids, such as α-amino phosphonic acids and α-amino phosphinic acids, or amino acids having non-peptide linkages, nucleic acids, nucleic acid analogs such as phosphorothioates or peptide nucleic acids ("PNAs"), hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose.

In one embodiment, a test compound identified by the methods of the present invention (see Example, below) and useful for treating or preventing diseases in mammals is a TAR RNA-binding compound. In a preferred embodiment, the TAR RNA-binding compound is selected from the group consisting of:

$H_2N$-(L)Lys-(D)Lys-(L)Asn-OH,
$H_2N$-(L)Lys-(D)Lys-(D)Asn-OH,
$H_2N$-(L)Lys-(L)Lys-(L)Asn-OH,
$H_2N$-(L)Arg-(D)Lys-(L)Asn-OH,
$H_2N$-(L)Arg-(D)Lys-(L)Val-OH,
$H_2N$-(L)Arg-(D)Lys-(L)Arg-OH,
$H_2N$-(D)Thr-(D)Lys-(L)Asn-OH, and
$H_2N$-(D)Thr-(D)Lys-(L)Phe-OH or a pharmaceutically acceptable salt thereof. Such test compounds are useful for treating or preventing HIV infection or AIDS in humans.

5.2 Target RNA-Dye Conjugates

Target RNAs useful in the methods of the present invention have a label that is detectable visually or via conventional spectroscopic means. Preferably, target RNAs are labeled with a covalently-attached dye molecule. Useful dye-molecule labels include, but are not limited to, fluorescent dyes, phosphorescent dyes, ultraviolet dyes, infrared dyes, and visible dyes. Preferably, the dye is a visible dye.

In a preferred embodiment, RNAs that are labeled at one or more specific locations are chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1–17; Users Manual Model 392 and 394 Polynucleotide Synthesizers, 1990, pages 6–1 through 6–22, Applied Biosystems, Part No. 901237). The phosphoramidite method of polynucleotide synthesis is the preferred method because of its efficient and rapid coupling and the stability of the starting materials. The synthesis is performed with the growing polynucleotide chain attached to a solid support, such that excess reagents, which are generally in the liquid phase, can be easily removed by washing, decanting, and/or filtration, thereby eliminating the need for purification steps between synthesis cycles.

The following briefly describes illustrative steps of a typical polynucleotide synthesis cycle using the phosphoramidite method. First, a solid support to which is attached a protected nucleoside monomer at its 3' terminus is treated with acid, e.g., trichloroacetic acid, to remove the 5'-hydroxyl protecting group, freeing the hydroxyl group for a subsequent coupling reaction. An activated intermediate is then formed by contacting the support-bound nucleoside with a protected nucleoside phosphoramidite monomer and a weak acid, e.g., tetrazole. The weak acid protonates the nitrogen atom of the phosphoramidite forming a reactive intermediate. Nucleoside addition is generally complete within 30 seconds. Next, a capping step is performed, which terminates any polynucleotide chains that did not undergo nucleoside addition. Capping is preferably performed using acetic anhydride and 1-methylimidazole. The phosphite group of the internucleotide linkage is then converted to the more stable phosphotriester by oxidation using iodine as the preferred oxidizing agent and water as the oxygen donor. After oxidation, the hydroxyl protecting group of the newly added nucleoside is removed with a protic acid, e.g., trichloroacetic acid or dichloroacetic acid, and the cycle is repeated one or more times until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and any protecting groups on the dyes are removed by treating the polynucleotide solution in base at an elevated temperature, e.g., at about 55° C . Preferably the various protecting groups are removed using ammonium hydroxide or t-butyl amine.

Any of the nucleoside phosphoramidite monomers can be labeled using standard phosphoramidite chemistry methods (see FIG. 3; Hwang et al. (1999) Proc. Natl. Acad. Sci. U.S.A. 96(23):12,997–13,002 and references cited therein). Dye molecules useful for covalently coupling to phosphoramidites preferably comprise a primary hydroxyl group that is not part of the dye's chromophore. Illustrative dye molecules include, but are not limited to, disperse dye CAS 4439-31-0, disperse dye CAS 6054–58–6, disperse dye CAS 4392-69-2 (Sigma-Aldrich, St. Louis, Mo.), disperse red, and 1-pyrenebutanol (Molecular Probes, Eugene, Oreg.). Other dyes useful for coupling to phosphoramidites will be apparent to those of skill in the art, and may be purchased from, e.g., Sigma-Aldrich, St. Louis, Mo. or Molecular Probes, Inc., Eugene, Oreg. Most preferably, one disperse red-labeled phosphoramidite is incorporated at the 5' end of the target RNA.

In another embodiment, dye-labeled target RNA molecules are synthesized enzymatically using in vitro transcription (Hwang et al. (1999) Proc. Nat'l Acad. Sci. USA 96(23):12,997–13,002 and references cited therein). In this embodiment, a template DNA is denatured by heating to about 90° C. and an oligonucleotide primer is annealed to the template DNA, for example by slow-cooling the mixture of the denatured template and the primer from about 90° C. to room temperature. A mixture of ribonucleoside-5'-triphosphates capable of supporting template-directed enzymatic extension of the primed template (e.g., a mixture including GTP, ATP, CTP, and UTP), including one or more dye-labeled ribonucleotides (Sigma-Aldrich, St. Louis, Mo.), is added to the primed template. Next, a polymerase enzyme is added to the mixture under conditions where the polymerase enzyme is active, which are well-known to those skilled in the art. A labeled polynucleotide is formed by the incorporation of the labeled ribonucleotides during polymerase-mediated strand synthesis.

In yet another embodiment of the invention, RNA molecules are end-labeled after their synthesis. Methods for labeling the 5' end of an oligonucleotide include but are by no means limited to: (i) periodate oxidation of a 5'-to-5'-coupled ribonucleotide, followed by reaction with an amine-reactive label (Heller & Morisson (1985) in *Rapid Detection and Identification of Infectious Agents*, D. T. Kingsbury and S. Falkow, eds., pp 245–256, Academic Press); (ii) condensation of ethylenediamine with 5'-phosphorylated polynucleotide, followed by reaction with an amine reactive label (Morrison, European Patent Application 232 967); and (iii) introduction of an aliphatic amine substituent using an aminohexyl phosphite reagent in solid-phase DNA synthesis, followed by reaction with an amine reactive label (Cardullo et al. (1988) *Proc. Natl. Acad. Sci. USA*, 85: 8790–8794).

A detectable label should not be incorporated into a target RNA at the specific ligand binding site at which test compounds are likely to bind, since the presence of a covalently attached label might interfere sterically or chemically with the binding of the test compounds at this site. Accordingly, if the region of the target RNA that binds to an in vivo ligand is known, a detectable label is preferably incorporated into the RNA molecule at one or more positions that are spatially or sequentially remote from the binding region.

After synthesis, the labeled target RNA can be purified using standard techniques known to those skilled in the art (see Hwang et al. (1999) Proc. Natl. Acad. Sci. U.S.A. 96(23):12,997–13,002 and references cited therein). Depending on the length of the target RNA and the method of its synthesis, such purification techniques include, but are not limited to, reverse-phase high-performance liquid chromatography ("reverse-phase HPLC"), fast performance liquid chromatography ("FPLC"), and gel purification. After purification, the target RNA is refolded into its native conformation, preferably by heating to approximately 85–95° C. and slowly cooling to room temperature in a buffer, e.g., a buffer comprising about 50 mM Tris-HCl, pH 8 and 100 mM NaCl.

5.3 Encoded Combinatorial Libraries

Combinatorial compound libraries useful for the methods of the present invention are preferably synthesized on solid supports. In one embodiment, a split synthesis method, a protocol of separating and mixing solid supports during the synthesis, is used to synthesize a library of compounds on solid supports (see Lam et al. (1997) Chem. Rev. 97:41–448; Ohlmeyer et al. (1993) Proc. Natl. Acad. Sci. USA 90:10, 922–10,926 and references cited therein). Each solid support in the final library has substantially one type of test compound attached to its surface. Other methods for synthesizing combinatorial libraries on solid supports, wherein one product is attached to each support, will be known to those of skill in the art (see, e.g., Nefzi et al. (1997) Chem. Rev. 97:449–472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (PMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In one embodiment, the solid phase support is suitable for in vivo use, i.e., it can serve as a carrier or support for administration of the test compound to a patient (e.g., TENTAGEL, Bayer, Tubingen, Germany). In a particular embodiment, the solid support is palatable and/or orally ingestable.

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of test compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In embodiments where readable molecular tags are cleaved from the solid support and analyzed to determine the structure of the library compound on the support (see below), the readable tags and the test compound can be attached to the solid support via one or more different types of linkers, such that the tags can be cleaved without removing the test compound from the support, and vice versa. Appropriate types of linkers useful in embodiments of the present invention will be known to those of skill in the art (see Guillier et al. (2000) Chem. Rev. 100:2091–2157).

The combinatorial libraries useful in the methods of the invention preferably comprise the types of compounds that will potentially bind to the ligand binding sites of the target RNAs used to screen them. For example, if TAR RNA is used to screen a library for test compounds that bind to TAR RNA's Tat binding site, the test compounds are preferably peptides or peptidomimetics that are structurally similar to the natural Tat peptide that binds TAR RNA with high affinity. A plurality of test compounds is preferably attached to each solid support such that, when dye-labeled target RNA molecules bind to the test compounds on the solid support, the solid support becomes labeled and can be separated from the unlabeled solid supports. Therefore, the synthesis of test compounds is preferably monitored so that each support has attached thereto substantially one type of test compound. In addition, the structure of the test compound attached to the dye-labeled solid support can be determined.

Libraries screened using the methods of the present invention can comprise a plurality of supports and accordingly, a variety of types of test compounds. In some embodiments, the test compounds are nucleic acid or peptide molecules. In other embodiments, types of test compounds include, but are not limited to, peptide analogs including peptides comprising non-naturally occurring amino acids, e.g., D-amino acids (see Table 1, below), phosphorous analogs of amino acids, such as α-amino phosphonic acids and α-amino phosphinic acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose.

A variety of techniques useful for determining the structures of test compounds on dye-labeled solid supports are useful in the methods of the invention. One skilled in the art will also recognize that these techniques can also be used to monitor synthesis of test compounds on the solid supports. As used herein, a library is "encoded" when one or more readable tags are attached to, or incorporated into, a solid support such that there is about a one-to-one correspondence between the identity of the one or more readable tags on the solid support and the structure of the test compound attached thereto. Those of skill in the art will readily appreciate that in some embodiments of the invention, the test compound itself is the readable tag. For example, if the structure of the test compound itself is determined using, e.g., nuclear magnetic resonance ("NMR") spectroscopy of the test compound either on the support or after cleavage, then, as used herein, the test compound is the readable tag. These embodiments of the invention use direct techniques for determining the structure of the test compound. In other embodiments of the invention, the one or more readable tags are distinct from the test compounds. In these embodiments, indirect techniques, e.g., techniques that identify of the one or more readable tags rather than determine the structure of the test compound itself, are used. The one-to-one correspondence between the identity of the one or more readable tags and the test compound on the solid support provides the structure of the test compound. As used herein, a solid support is "decoded" when the identity of the one or more readable tags on the support is determined using either direct or indirect techniques.

A variety of direct techniques for determining the structure of test compounds on solid supports are useful in the methods of the invention. In embodiments where the test compound is a peptide or oligonucleotide, the structure of these compounds can be determined by standard peptide or oligonucleotide sequencing techniques, respectively. In some embodiments, the library will not comprise test compounds wherein structures can be determined by sequencing techniques, since the test compounds are not limited to peptides or nucleic acids. In some embodiments, structures of test compounds are determined using NMR techniques, such as high resolution magic angle spinning NMR spectroscopy (Warrass et al. (1999) J. Am. Chem. Soc. 121:3787–3788). In these embodiments, the test compounds are not cleaved from the solid support, thus eliminating an extra chemistry step that may destroy them. Instead, NMR spectra of support-bound test compounds are collected and sophisticated solvent suppression techniques are applied based on differential diffusion behavior of solvent and compounds attached to the solid supports, which allow for greater signal-to-noise ratios and resolution in the spectra.

In other embodiments, Fourier transform infra-red spectroscopy (FTIR) or Fourier transform Raman spectroscopy (FT-Raman) can be used to decode a solid support by determining structure of the test compound bound thereto (Yan et al. (1999) J. Comb. Chem. 1:46–54). The advantage of these techniques is that they are sensitive to changes in organic functional groups and can be performed on a single solid support. In still other embodiments, electrospray ionization (ESI) mass spectrometry or matrix-assisted laser desorption/ionization (MALDI) mass spectrometry, either alone or coupled with HPLC or other separation techniques, are used in the methods of the invention (Süβmuth et al. (1999) J. of Chromatography B 725:49–65). The mass spectrometry methods are sensitive methods requiring only small amounts of sample that can be the test compounds either after cleavage or while on the solid support. In yet other embodiments, X-ray photoelectron spectroscopy is used to identify the structure of test compounds (Yoo et al. (1999) J. Comb. Chem. 1(3):177–180). This technique utilizes a resin modified with a suitable heteroatom, such as bromine, which interacts with heteroatoms in the test compound being synthesized in order to monitor, e.g., coupling efficiencies and reaction times, or to identify products of a synthesis.

Indirect techniques for determining the structure of a test compound on a solid support involve decoding one or more readable tags on the solid support that do not include the test compound itself, but that have about a one-to-one correspondence with a particular test compound, such that identification of one or more tags associated with a solid support unequivocally identifies the structure of the test compound.

In a preferred embodiment, test compounds are synthesized on a solid support, and during each step of the synthesis, readable molecular tags that encode the step number and the chemical reagent used in that step are attached to the support (Ohlmeyer et al. (1993) Proc. Natl. Acad. Sci. USA 90:10,922–10,926; Still (1996) Acc. Chem. Res. 29:155–163). In this embodiment, the readable tags provide a history of the synthesis as well as identify the test compound on the support. The tags are cleaved from the solid support and read by, e.g., electron capture gas chromatography, in order to decode the support. Different types of readable molecular tags useful in embodiments of the present invention that employ readable molecular tags to decode solid supports will be apparent to those skilled in the art and include oligonucleotides, peptides and small organic molecules (see Nefzi et al. (1997) Chem. Rev. 97:449–472; Lam et al. (1997) Chem. Rev. 97:411–448).

In other embodiments, decoding a solid support involves the use of laser optical synthesis chips (LOSCS) (Xiao et al. (1997) Angew. Chem. Int. Ed. Engl. 36(7):780–782). This technology does not involve the use of chemical tags, but rather bar codes etched into the solid support with a laser. If each bar code is associated with a particular test compound, reading the bar code on the solid support will identify the structure of the test compound attached to the solid support. In still other embodiments, fluorescently labeled solid supports can be used for the synthesis of a library of test compounds, and the fluorescence spectra of the fluorescent labels can be used to identify the structure of the test compounds thereon (Yan et al. (1998) J. Comb. Chem. 1(1):78–81).

5.4 Screening of a Library with a Dye-Labeled Target RNA

After a target RNA is labeled and a combinatorial test compound library is synthesized, the dye-labeled target RNA is used to screen the library to identify test compounds that bind to the RNA. Screening comprises contacting a dye-labeled target RNA with a solid support to which a test compound is attached. Preferably, the contacting occurs in an aqueous solution. The aqueous solution preferably stabilizes the dye-labeled target RNA and prevents RNA denaturation or degradation without interfering with binding of the test compounds. The aqueous solution is preferably similar to the solution in which a complex between the target RNA and its natural ligand is formed in vitro. For example, TK buffer, which is commonly used to form Tat protein-TAR RNA complexes in vitro, is preferably used in the methods of the invention as an aqeuous solution to screen a library of test compounds for TAR RNA binding compounds (see Example, below).

The methods of the present invention for screening a library of test compounds attached to one or more solid supports preferably comprise contacting a test compound with a target RNA in the presence of an aqueous solution, the aqueous solution comprising a buffer and a combination of salts. The aqueous solution optionally further comprises unlabeled target RNA having a mutation at the ligand binding site, which renders the unlabeled RNA incapable of interacting with a test compound at that site. For example, if dye-labeled TAR RNA is used to screen a library, unlabeled TAR RNA having a mutation in the uracil 23/cytosine 24 bulge region is also present in the aqueous solution. Without being bound by any theory, the addition of unlabeled RNA that is essentially identical to the dye-labeled target RNA except for a mutation at the ligand binding site might minimize interactions of other regions of the dye-labeled target RNA with test compounds or with the solid support and prevent false positive results.

The solution further comprises a buffer, a combination of salts, and optionally, a detergent or a surfactant. The pH of the solution typically ranges from about 5 to about 8, preferably from about 6 to about 8, most preferably from about 6.5 to about 8. A variety of buffers may be used to achieve the desired pH. Suitable buffers include, but are not limited to, Tris, Mes, Bis-Tris, Ada, Aces, Pipes, Mopso, Bis-Tris propane, Bes, Mops, Tes, Hepes, Dipso, Mobs, Tapso, Trizma, Heppso, Popso, TEA, Epps, Tricine, Gly-Gly, Bicine, and sodium-potassium phosphate. The solution comprises from about 10 mM to about 100 mM, preferably from about 25 mM to about 75 mM, most preferably from about 40 mM to about 60 mM buffer. The pH of the aqeuous solution can be optimized for different screening reactions, depending on the target RNA used and the types of test compounds in the library, and therefore, the type and amount of the buffer used in the solution can vary from screen to screen. In a preferred embodiment, the aqueous solution has a pH of about 7.4, which can be achieved using about 50 mM Tris buffer.

In addition to an appropriate buffer, the aqueous solution further comprises a combination of salts, from about 2 mM to about 20 mM KCl, from about 1 mM to about 100 mM NaCl, and from about 0 mM to about 20 mM $MgCl_2$. Without being bound by any theory, Applicant has found that a combination of KCl, NaCl, and $MgCl_2$ stabilizes the target RNA such that most of the RNA is not denatured or digested over the course of the screening reaction. The optional concentration of each salt used in the aqueous solution is dependent on the particular target RNA used and can be determined using routine experimentation.

The solution optionally comprises from about 0.01% to about 0.5% (w/v) of a detergent or a surfactant. Without being bound by any theory, a small amount of detergent or surfactant in the solution might reduce non-specific binding of the target RNA to the solid support and control aggregation and increase stability of target RNA molecules. Typical detergents useful in the methods of the present invention include, but are not limited to, anionic detergents, such as salts of deoxycholic acid, 1-heptanesulfonic acid, N-laurylsarcosine, lauryl sulfate, 1-octane sulfonic acid and taurocholic acid; cationic detergents such as benzalkonium chloride, cetylpyridinium, methylbenzethonium chloride, and decamethonium bromide; zwitterionic detergents such as CHAPS, CHAPSO, alkyl betaines, alkyl amidoalkyl betaines, N-dodecyl-N,N-dimethyl-3-ammonio-1-propanesulfonate, and phosphatidylcholine; and non-ionic detergents such as n-decyl α-D-glucopyranoside, n-decyl β-D-maltopyranoside, n-dodecyl β-D-maltoside, n-octyl β-D-glucopyranoside, sorbitan esters, n-tetradecyl β-D-maltoside and tritons. Preferably, the detergent, if present, is a nonionic detergent. Typical surfactants useful in the methods of the present invention include, but are not limited to, ammonium lauryl sulfate, polyethylene glycols, butyl glucoside, decyl glucoside, Polysorbate 80, lauric acid, myristic acid, palmitic acid, potassium palmitate, undecanoic acid, lauryl betaine, and lauryl alcohol. More preferably, the detergent, if present, is Triton X-100 and present in an amount of about 0.1% (w/v).

Non-specific binding of a dye-labeled target RNA to test compounds or to the solid support can be further minimized by pre-treating the combinatorial library with one or more blocking agents. In one embodiment, the combinatorial library is treated with a blocking agent, e.g., bovine serum albumin ("BSA"), before contacting with to the dye-labeled target RNA. In another embodiment, the combinatorial library is treated sequentially with at least two different blocking agents. In a preferred embodiment, the combinatorial library is suspended in a solution comprising BSA and is washed with a BSA-free solution (not containing BSA) to remove unbound BSA. This blocking step is preferably performed at room temperature for from about 0.5 to about 3 hours. In a subsequent step, the library is suspended in a solution comprising unlabeled RNA having a mutation at the ligand binding site. This blocking step is preferably performed at about 4° C. for from about 12 hours to about 36 hours. Finally, the library is washed an RNA-free solution (not containing RNA) in order to remove unbound unlabeled RNA. Preferably, the solution used in the one or more blocking steps is substantially similar to the aqueous solution used to screen the library with the dye-labeled target RNA, e.g., in pH and salt concentration.

Once contacted, the mixture of dye-labeled target RNA and the test compound is preferably maintained at 4° C. for from about 1 day to about 5 days, preferably from about 2 days to about 3 days with constant stirring. The solid support is subsequently washed, and labeled solid supports are identified. To identify other test compounds in the library that bind less tightly to the target RNA, the one or more solid supports can subsequently be exposed to additional dye-labeled target RNA for from about 1 day to about 3 days longer and additional labeled solid supports identified.

The methods for identifying labeled solid supports will vary with the type of label on the target RNA. For example, if the target RNA is labeled with a visible dye, labeled solid supports are preferably identified using visual inspection, e.g., under a microscope using a micropipet. If the label is fluorescent, then solid supports that become fluorescent with bound dye-labeled target RNA are identified using, e.g., a fluorescence activated cell sorter. Methods for identifying different types of labels on target RNAs are well known. In a preferred embodiment, a visible label is used and solid supports that acquire the color of the dye are identified using visual inspection and separated from the remaining, colorless solid supports using a micro capillary pipet. The structures of the test compounds on the chosen solid supports are determined by decoding the solid support, as discussed above in Section 5.3.

6. EXAMPLE

Identification of TAR RNA-Binding Tripeptides

6.1 Materials and Methods

Preparation of an encoded combinatorial library. A tripeptide library was prepared on TENTAGEL (TentaGel S-NH2 from Rapp Polymere, Tübingen, Germany (Bayer, E. (1991) *Angew. Chem.* 30, 113–129)) using encoded splitsynthesis (Ohlmeyer et al. (1993) *Proc. Natl. Acad. Sci. USA* 90, 10922–10926). The library had the general structure Ac-AA3-AA2-AA1-NH(CH$_2$)$_2$-O-TENTAGEL, and contained the following amino acids: Gly, D-Ala, L-Ala, D-Val, L-Val, D-Leu, L-Leu, D-Pro, L-Pro, D-Phe, L-Phe, D-Gln, L-Gln, D-Asn, L-Asn, D-Lys, L-Lys, D-His, L-His, D-Arg, L-Arg, D-Glu, L-Glu, D-Asp, L-Asp, D-Ser, L-Ser, D-Thr, and L-Thr. The library did not contain Cys, Trp, Tyr, Met or Ile. The library was encoded using a set of 15 photocleavable tags (5 GC-separable tags comprising a hydrocarbon chain and an aromatic electrophore per amino acid). After the synthesis of the library was complete, test compound side chains were deprotected with trifluoroacetic acid. One copy of the library contained all 24,389 possible tripeptide sequences (29$^3$ tripeptides were synthesized using 29 amino acids).

RNA synthesis using phosphoramidite chemistry. Dyelabeled TAR RNA was synthesized on an Applied Biosystems Model 392 DNA/RNA synthesizer using 2-cyanoethyl phosphoramidite chemistry. All (2-cyanoethyl) phosphoramidite monomers were obtained from Glen Research (Sterling, Va.). Disperse red phosphoramidite (FIG. 3) (0.15 M solution in CH$_3$CN) was used to incorporate a dye label at the 5'-end of TAR RNA (SEQ. ID. NO. 1). Synthesis of the disperse red phosphoramidite (FIG. 3) was accomplished according to standard phosphoramidite chemistry methods (Scaringe et al. (1990) *Nucl. Acids Res.* 18, 5433–41; Shah et al. (1994) *Bioconjugate Chem.* 5, 508–512; Misiura et al. (1990) *Nucl. Acids Res.* 18, 4345–54). RNA (1 μmole) labeled with disperse red was deprotected by treatment with NH$_3$-saturated methanol (2 mL) at 25° C. for 17 hours. The resulting product was filtered and dried in a Speedvac lyophilizer (Savant). To deprotect 2'-OH silyl groups, the red pellet comprising dye-labeled RNA was dissolved in 50% triethylamine trihydrofluoride in dimethyl sulfoxide (0.5 mL) and left at room temperature for 16 hours. Deprotected RNA was precipitated by the addition of 2 mL of isopropyl alcohol. After deprotection, RNA was purified and characterized as described previously (Shah et al. (1994) *Bioconjugate Chem.* 5, 508–512; Shah et al. (1996) *Bioconjugate Chem.* 7, 283–289; Ping et al. (1997) *RNA* 3, 850–860).

Unlabeled RNA synthesis by in vitro transcription (Milligan et al. (1987) *Nucl. Acids Res.* 15, 8783–8798; Wang, Z. & Rana, T. M. (1996) *Biochemistry* 35, 6491–6499). All template and primer DNAs were synthesized on an Applied Biosystems ABI 392 DNA/RNA synthesizer. The template strands (SEQ. ID. NO. 3 and SEQ. ID. NO. 4, respectively) encode the sequences for wild-type TAR RNA (SEQ. ID. NO. 1) or bulge mutant (SEQ. ID. NO. 5) TAR RNA, e.g., a TAR RNA lacking the natural 3-nucleotide bulge. The top strand primer is a short piece of DNA complementary to the 3' end of all template DNAs having the sequence 5'TAATACGACTCACTATAG3' (SEQ. ID. NO. 6). The template DNA was annealed to an equimolar amount of top strand DNA and transcribed using T7 RNA polymerase in transcription buffer (40 mM Tris-HCl, pH 8.1, 1 mM spermidine, 0.01% Triton X-100, 5 mM DTT) and 4.0 mM NTPs at 37° C. for 2–4 ours. For 20 μL reactions containing 8.0 pmoles template DNA, 40–60 units of T7 RNA polymerase (Promega) were used. Transcription reactions were stopped by adding an equal volume of sample loading buffer. TAR RNA (SEQ. ID. NO. 1) or bulge mutant TAR RNA (SEQ ID. NO. 5) was purified on 20% acrylamide 8M-Urea denaturing gels and stored in DEPC water at −20° C. Unlabeled RNAs were used in the screening assay as described below.

Enzymatically transcribed RNAs were 5' dephosphorylated by incubation with calf intestinal alkaline phophatase (Promega) for one hour at 37° C. in 50 mM Tris-Cl, pH 9.0, 1 mM MgCl$_2$, 0.1 mM ZnCl$_2$, 1 mM spermidine. The RNAs were purified by multiple extractions with Tris-saturated phenol and one extraction with 24:1 chloroform:isoamyl alcohol, followed by ethanol precipitation. The RNAs were labeled at the 5'-end with 0.5 μM [γ-$^{32}$p] ATP (6000 Ci/mmol) (ICN) per 100 pmoles RNA by incubating with 16 units T4 polynucleotide kinase (New England Biolabs) in 70 mM Tris-HCl, pH 7.5, 10 mM MgC12, 5 mM DTT (Wang, Z. & Rana, T. M. (1996) *Biochemistry* 35, 6491–6499; Neenhold, H. R. & Rana, T. M. (1995) *Biochemistry* 34, 6303–6309). The RNAs were labeled at the 3'-end by ligation to cytidine 3',5'-[5'-$^{32}$P]bisphosphate ([$^{32}$P]pCp) using T4 RNA ligase. Reaction mixtures (50 μL) contained 250 pmol RNA, 65 μCi [$^{32}$P]pCp (3000 Ci/mmol, NEN™, Boston, Mass.), and 40 units T4 RNA ligase (New England Biolabs) in a buffer containing 50 mM Tris-HCl (pH 8.0), 3 mM DTT, 10 mM MgCl$_2$, 25 mM NaCl, 50 mM ATP, 25 μg/mL bovine serum albumin, and 10% dimethylsulfoxide (v/v). After incubation at 4° C. overnight, the labeled RNAs were purified using phenol-chloroform extraction and ethanol precipitation. 3'- and 5'-end-labeled RNAs were purified on a denaturing gel, visualized by autoradiography, eluted out of the gels, and desalted on a reverse-phase cartridge.

The sequences of RNAs were determined by base hydrolysis and nuclease digestion. Alkaline hydrolysis of RNAs was carried out in hydrolysis buffer for 8–12 minutes at 85° C. RNAs were incubated with 0.1 units RNAse from *B. cereus* (Pharmacia) per pmole RNA for 4 minutes at 55° C. in 16 mM sodium citrate, pH 5.0, 0.8 mM EDTA, 0.5 mg/ml yeast tRNA (Gibco-BRL). This enzyme yields U- and C-specific cleavage of RNA. Sequencing products were resolved on 20% denaturing gels and visualized by phosphor image analysis.

Screening the librara with TAR RNA. Three copies of the tripeptide library on encoded beads, which contain more than 95% of the members of the library, were placed in an eppendoff tube and washed with water (500 μL×5) and TK buffer (50 mM Tris-HCl (pH 7.4), 20 mM KCl, 0.1% Triton X- 100) (500 μL×4), which is commonly used for the formation of Tat-TAR complexes in vitro (Churcher et al. (1993) *J. Mol. Biol.* 230, 90–110). After filtration, the beads were suspended in TK buffer (400 μL) and bovine serum albumin (0.1 mg/mL) at room temperature for 1 hour to reduce nonspecific binding. The aqueous phase was removed, and the beads were washed with TK buffer (500 μL×3). After filtration, the beads were resuspended in 600 mL TK buffer, 2.5 μM of bulge mutant TAR RNA was added, and the suspension was stirred at 4° C. for 1 day. The buffer was removed, the beads were resuspended in 600 mL TK buffer, and 250 nM disperse red-dye-labeled-TAR RNA and 2.5 μM bulge mutant TAR RNA were added. After 2 days of stirring at 4° C., the buffer was removed, and the remaining beads were washed with water (500 μL×3). Two red beads were picked under a microscope and placed in separate capillary tubes. The remaining beads were further incubated with a mixture of disperse-red-dye-labeled TAR RNA and bulge mutant TAR RNA for 3 days, as described above. During the second screening, eight beads turned red. These beads were picked and placed in capillary tubes.

Decoding the structures of RNA-binding ligands. A disperse-red dye labeled encoded bead was placed in a 25 μL micro capillary tube containing dimethylformamide (DMF) (2 μL) and the bead was washed with DMF (5 μL×4). After draining the solvent, the bead was resuspended in 2 μL DMF and the micro capillary tube was centrifuged for 4 min and then flame sealed. Each capillary tube containing a bead was then irradiated with UV radiation at 350 nm for 4 hours and spun for 5 minutes in a centrifuge. The capillary tube was opened and the cleaved tag alcohols were silylated with N, O-bis(trimethylsilyl)acetamide in a micro syringe. The N, O-bis(trimethylsilyl)acetamide derivatives (1 μL) were analyzed using electron capture gas chromatography ("ECGC"). A Hewlett Packard 6890 series Gas Chromatography system, equipped with a micro electron capture detector (μ-ECD) and a HP Chemstation operating system, was used for all decoding analyses. The GC was operated in splitless inlet mode, using helium as the carrier gas. A 35 m×0.2 mm i.d.×0.33 μm film thickness HP-Ultra 1 column was used with a temperature program of 1 min isothermal at 200° C. followed by heating at 10° C./min to 320° C. The μ-ECD make up gas was nitrogen. The structures of TAR RNA binding compounds decoded as detailed in this section are shown in Table 1.

TABLE 1

RNA-binding Ligands

| ID # | Structures | Freq-uency | Color | $K_D$, nM | $K_{REL}$ |
|---|---|---|---|---|---|
| 1 | $H_2N$-(L)Lys-(D)Lys-(L)Asn-OH | 2 | Red | 420 ± 44 | 1.73 |
| 2 | $H_2N$-(L)Lys-(D)Lys-(D)Asn-OH | 1 | Pink | 4,173 ± 208 | 0.17 |
| 3 | $H_2N$-(L)Lys-(L)Lys-(L)Asn-OH | 2 | Pink | 3,224 ± 183 | 0.23 |
| 4 | $H_2N$-(L)Arg-(D)Lys-(L)Asn-OH | 1 | Pink | 2,640 ± 219 | 0.28 |
| 5 | $H_2N$-(L)Arg-(D)Lys-(L)Val-OH | 1 | Pink | 10,434 ± 594 | 0.07 |
| 6 | $H_2N$-(L)Arg-(D)Lys-(L)Arg-OH | 1 | Pink | 878 ± 80 | 0.83 |
| 7 | $H_2N$-(D)Thr-(D)Lys-(L)Asn-OH | 1 | Pink | 564 ± 80 | 1.29 |
| 8 | $H_2N$-(D)Thr-(D)Lys-(L)Phe-OH | 1 | Pink | 2,087 ± 244 | 0.35 |

$K_D$ values were determined from four independent experiments.
$K_{REL} = K_D$ of a basic Tat peptide (727 ± 74 nM)/$K_D$ of Inhibitor.
The bead library peptides all were N-acetylated. Peptides used for in vitro and in vivo experiments were not N-acetylated and contained free amino terminal.

Solid-phase RNA-peptide binding assays. TAR RNA binding compounds found and decoded as described above (shown in Table 1) were synthesized on TENTAGEL S-$NH_2$ (4.6 μmole). All fluorenylmethoxycarbonyl (Fmoc)-protected amino acids were purchased from Bachem (Torrance, Calif.). 1-hydroxybenzotriazole (HOBT) and diiopropylcarbodiimide (DIPCDI) were obtained from Aldrich Chemical Co., Milwaukee, Wis. Piperidine and trifluoroacetic acid were purchased from Applied Biosystems Division, Perkin-Elmer. All ligands were synthesized manually according to standard solid-phase peptide synthesis protocols. Coupling efficiencies of residues at each step were monitored using a standard Kaiser test. Deprotection of tripeptides was carried out in 10% water in trifluoroacetic acid (1 mL) for 16 hours at room temperature. After filtration of solvents, the resin was washed with water (1 mL×4), DMF (1 mL×4), and dichloromethane (1 mL×4), and dried under reduced pressure. Ten beads with attached tripeptides were placed in an Eppendorff tube and washed with TK buffer (200 gL×3). The beads were suspended in TK buffer (300 μL) and incubated with TAR RNA (1.95 μM) overnight at 4° C. The suspension was spun in a centrifuge, and the supernatant containing unbound RNA was transferred to a cuvette for optical density measurements at 260 nm using a Shimadzu UV-1601 spectrometer. Equilibrium concentrations of RNA were determined from these measurements. Given that the initial concentrations of ligand and RNA are known, and assuming simple bimolecular receptor/substrate binding, a dissociation constant ($K_D$) was calculated from known equations in order to determine which test compounds bind TAR RNA most tightly.

Inhibition of Tat trans-activation in cellular assays. HL3T1 cells, a HeLa cell line derivative containing an integrated HIV-1 LTR promoter and CAT reporter gene, were used for this assay. Cells were grown in 2 mL of Dulbecco's modified Eagle medium (DMEM) supplemented with 10% fetal calf serum in 60 mm dishes at 37° C. in 5% $CO_2$ in a tissue culture incubator. Cells were refreshed by 2 mL DMEM before transfection. Transfection was started by dropwise addition of 250 μL 2×Hepes-buffered saline and maintenance at room temperature for 10 minutes. Approximately 10 μg of plasmids (pSV2Tat and pAL) and increasing amounts of tripeptide 1 were transfected in the presence of $CaCl_2$ (final concentration 125 mM) and the cells were incubated for 4 hours at 37° C. in a tissue culture incubator. The medium was then discarded and the cells were subjected to glycerol shock (1.5 mL of 15%) for 45 seconds. Finally, the cells were washed twice with 5 mL phosphate-buffered saline (PBS) and were grown in 3 mL DMEM. DMEM was changed at 24 hours post-transfection, and cells were harvested 48 hours post-transfection. Cells were lysed in reporter lysis buffer (Promega). Aliquots were used for CAT and luciferase assays. Both activities were normalized to protein concentration determined by using a modified Bradford assay (Bio-Rad).

6.2 Results

On-bead selection of structure-specific TAR RNA binding compounds. To identify tripeptides that bind to TAR RNA, the dye disperse red was covalently attached to TAR RNA, and the labeled RNA was incubated in a suspension of library beads made using the split synthesis method. Diffusion of low molecular weight target molecules into a bead of TENTAGEL resin is known to be rapid, whereas one might expect that a protein or large nucleic acid might be excluded from the bead interior, where the bulk of the tripeptide is displayed. Nevertheless, the dye-TAR RNA conjugate was able to enter the beads and bind in a structure-dependent manner to tripeptides attached thereto. The red color of the dye was clearly evenly distributed throughout the translucent bead. Broken beads were not selected. Peptides specific for portions of TAR RNA other than the bulge region were blocked using a relatively large concentration of an unlabeled bulge mutant TAR RNA. A small amount of detergent and low RNA concentrations (250 nM) also minimized non-specific binding.

Figure 4A:
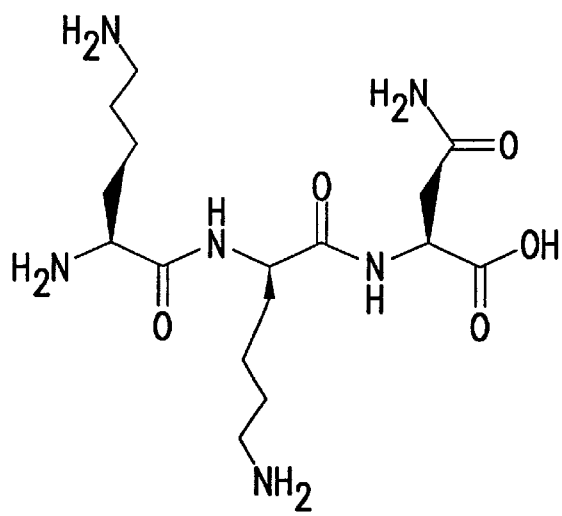
FIG. 4A shows the structure of tripeptide ID#1 (Table 1)

Ligand Sequence Analysis. Upon incubating the dye-TAR RNA conjugate with the library, only two beads were stained red. These two beads were separated from the rest of the library, which was allowed to incubate with the dye-TAR RNA conjugate for 3 days at 4° C. The initial two beads were found to contain the same sequence, (L)Lys-(D)Lys-(L)Asn (tripeptide ID# 1 in Table 1; FIG. 4(a)). At the end of the second incubation, only eight additional beads were stained pink-red. These beads were picked and decoded and the tripeptide sequences are listed in Table 1.

To verify that this assay reflected RNA-tripeptide interactions and to determine the affinity of these tripeptides for TAR RNA, the eight tripeptides were resynthesized and their dissociation constants with wild-type TAR RNA were measured. The results shown in Table 1 confirm that the on-bead assay mimics RNA binding because tripeptide ID# 1 has he highest affinity for TAR RNA ($K_D$=441 nM). To compare the RNA binding affinities of 8 ligands to natural Tat peptide, a Tat-derived peptide (Gly48 to Arg57) containing the RNA-binding region of Tat protein was synthesized (FIG. 2(b)) (SEQ. ID. NO. 2). The dissociation constant of the Tat peptide-RNA complex was determined under the same conditions used for the tripeptide-RNA complexes. These experiments showed that the Tat peptide binds TAR RNA with a $K_D$ of 698 nM. A relative dissociation constant ($K_{REL}$) can be calculated as the ratios of the Tat peptide to tripeptide dissociation constants ($K_D$) for TAR RNA. These results are shown in Table 1. Tripeptide ID #1 binds TAR RNA with affinities higher than the wild-type Tat peptide. These results indicate that selection frequency reflects ligand activity and, if a large enough library sample is used, could be used as an indicator of ligand affinity for RNA.

Several control experiments further supported these observations and demonstrated the specificity of tripeptide-TAR RNA interactions. First, incubating the library with free dye did not stain any beads, indicating that there was no interaction between the tripeptides of Table 1 and the dye molecule. Second, the equilibrium interaction between dye-labeled TAR RNA and a tripeptide tethered to beads was examined by incubating a suspension of beads containing tripeptide ID# 1 in TK buffer (400 $\mu$L) with dye-labeled TAR RNA (1 $\mu$M) at 4° C. for 5 hours. Beads were stained red upon TAR RNA binding. The interaction between dye-labeled TAR RNA and tripeptide ID # 1 is reversible and can be abolished by the addition of unlabeled TAR RNA or tripeptide ID# 1 as a competitor. Finally, screening the library with dye-labeled TAR RNA was carried out in the presence of excess unlabeled bulge mutant TAR RNA, inhibiting non-specific TAR RNA-peptide interactions.

As shown in Table 1, the complexes of TAR RNA with tripeptide ID# 1 ((L)Lys-(D)Lys-(L)Asn) and tripeptide ID# 7 ((D)Thr-(D)Lys-(L)Asn) had the lowest dissociation constants, suggesting a consensus sequence of X-(D)Lys-(L)Asn for tripeptides that inhibit Tat-TAR RNA interactions. Furthermore, tripeptides ID# 2 and ID# 3, and two diastereomers of tripeptide ID# 1 were found in the assay, ID# 3 being the only homochiral sequence. RNA-peptide binding measurements revealed that the dissociation constants for these two diastereomeric sequences were approximately 7 times higher than for tripeptide ID# 1. This sharp loss of binding energy among diastereomers indicates that the binding interaction is highly stereospecific and not merely the result of a non-specific lysine-phosphate backbone attraction. This is not surprising since the TAR RNA and hence the binding site, is necessarily chiral. Another interesting feature of these results is that all but one of the TAR RNA-binding sequences found were heterochiral, and therefore, would have been missed by other techniques such as phage-display, which only use the proteinogenic amino acids. Use of D- and L-amino acids together yields a richer stereochemical variety of ligands, in addition to the diversity imparted by using the $\alpha$-amino acids.

Figure 4B:
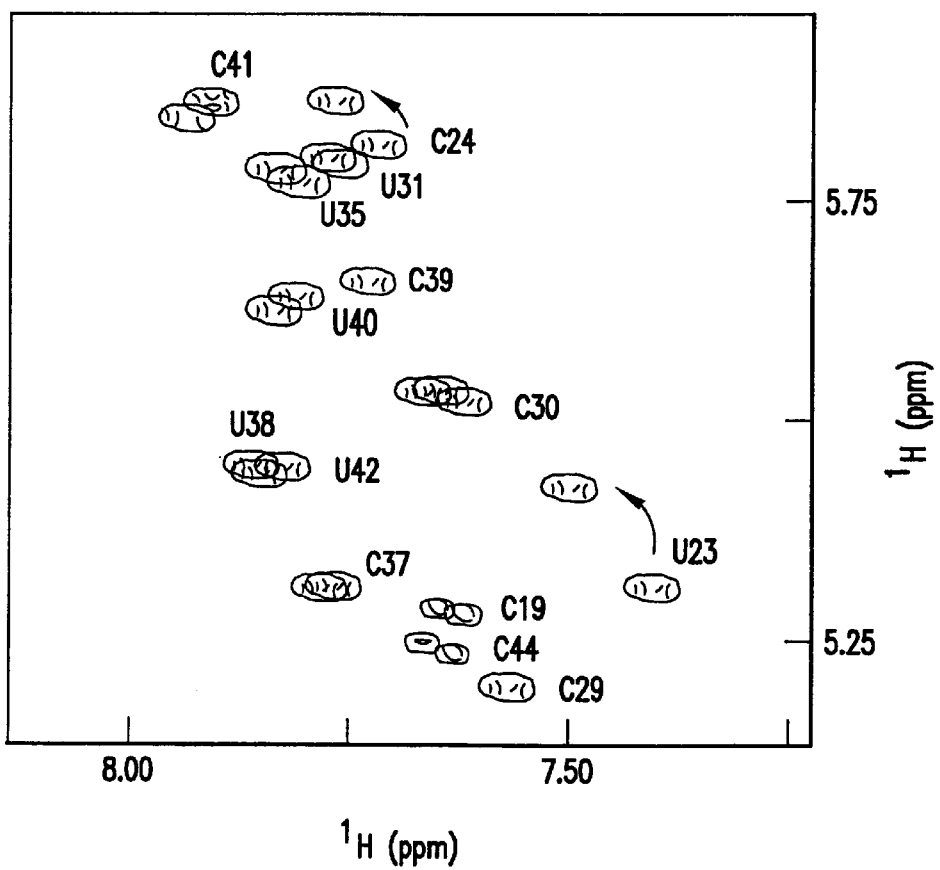
FIG. 4B shows the superposition of TOCSY NMR spectra of wild-type TAR RNA exposed to increasing amounts of tripeptide ID#1.

NMR Spectroscopy. NMR experiments were performed to determine the interaction sites of tripeptide ID# 1 on TAR RNA. NMR spectra of free TAR RNA and TAR RNA complexed with tripeptide ID# 1 were recorded. Due to the spectral overlap, it was impossible to follow all but a few well-isolated resonances by conventional 1-dimensional experiments. Therefore, two-dimensional NOESY and TOCSY experiments were performed. All spectra were recorded on a Bruker AMX-500 NMR spectrometer operating at 500 MHz for $^1$H equipped with triple resonance probe and H-broadband inverse detection probes. The ID and 2D $^1$H spectra were recorded at approximately 1 to 2 mM RNA and tripeptide ID# 1 concentrations in 5 mM phosphate buffer (pH 5.5), with up to 100 mM NaCl. All other conditions were the same as described earlier by Aboul-ela et al. ((1995) *J. Mol. Biol.* 253, 313–332.). Complete TAR RNA assignments were obtained. Increasing amounts of tripeptide 1 were added to TAR RNA and the spectral changes were monitored by two-dimensional TOCSY experiments. The TOCSY spectrum contains a region where only pyrimidine H5-H6 resonances are found; this region has a well-dispersed 2D spectrum. Resonances in the free RNA and RNA-ligand complexes were assigned by NOESY experiments. Results of the TOCSY experiments are shown in FIG. 4(b). Resonances in the bulge region, U23 and C24, were shifted. All other resonances were not affected significantly by the addition of the ligand. To address the question of whether spectral changes at U23 and C24 were due to specific tripeptide ID# 1 binding or whether they were the result of perturbation by a non-specific exogenous ligand, NMR experiments were performed in the presence of a basic tripeptide containing L-Lys amino acids. The results showed that the Lys- peptide did not cause shift of resonances in the bulge region including U23 and C24, indicating that tripeptide ID# 1 specifically interacts with TAR RNA at the bulge region. Interestingly, tripeptide ID# 1-TAR RNA interactions are different from TAR RNA-peptide or TAR RNA-Arg complexes reported in previous NMR studies (Aboul-ela et al. (1995) *J. Mol. Biol.* 253, 313–332; Puglisi et al. (1992) *Science* 257, 76–80) because there were no detectable interactions with the G26 and A27 regions as observed in those studies. Another TAR RNA-binding ligand that contains Arg side-chains also causes a conformational change in TAR RNA, resulting in a TAR RNA structure that is similar to the RNA structure in the TAR RNA-tripeptide complex (Hamy et al. (1997) *Proc. Natl. Acad. Sci. USA* 94, 3548–3553.). These results indicate that tripeptide ID# 1 is the first ligand that binds specifically to the bulge of TAR RNA in a manner different from previously reported TAR ligands and Tat peptides. These findings suggest an intriguing possibility that small molecules that interact with TAR RNA and induce a conformational change in the RNA resulting in a structure different from that the RNA in the Tat-TAR RNA complex could be used to lock TAR RNA into a non-functional structure and show that tripeptides ID# 1–8 are useful for treating or preventing HIV or AIDS in a patient.

Figure 5A:
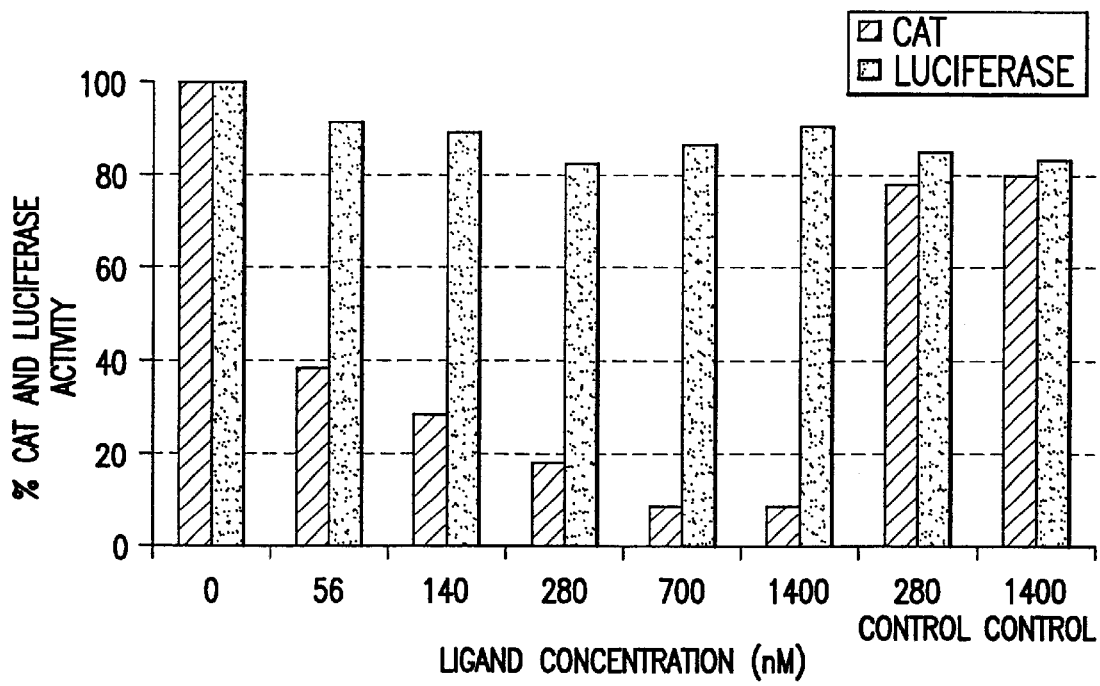
FIG. 5A shows the inhibition of Tat transactivation in HL3T1 cells with increasing concentrations of tripeptide ID#1.
Figure 5B:
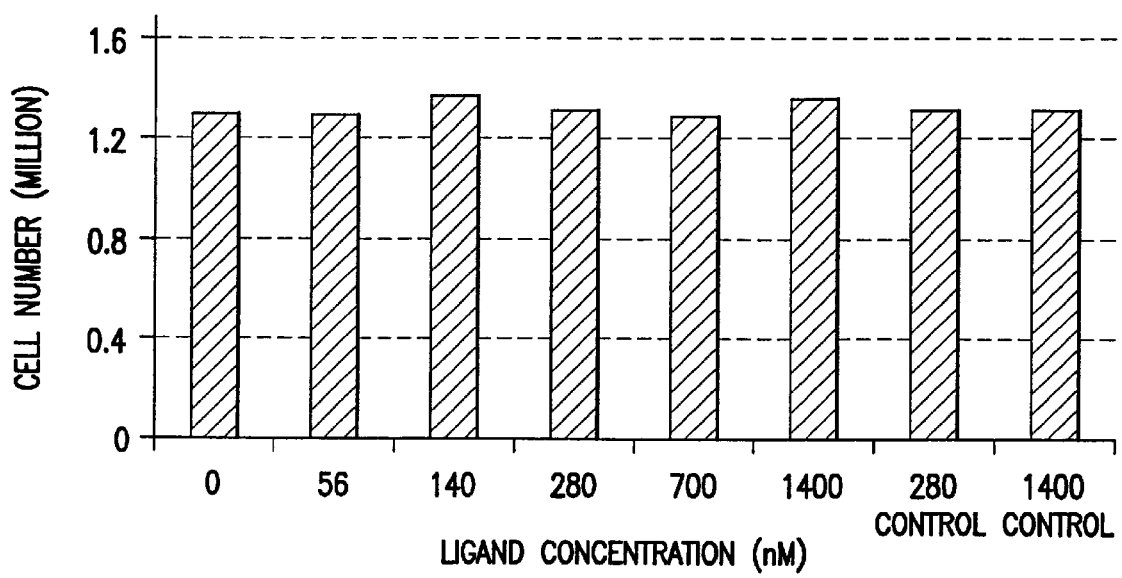
FIG. 5B shows that the number of cells assayed per ligand concentration in FIG. 5(a) remains virtually constant.

Inhibition of Tat trans-activation in vivo. To test whether the tripeptide 1- TAR RNA interaction could be used to control HIV-1 gene expression in vivo, HL3T1 cells, a HeLa cell line derivative containing an integrated HIV-1 LTR promoter and CAT reporter gene (Felber & Pavlakis (1988) *Science* 239, 184–187), were used. Different amounts of tripeptide ID# 1 were added during transfection of pSV2-Tat (Frankel & Pabo (1988) *Cell* 55, 1189–1194) and pAL (Nordeen (1988) *Biotechniques* 6, 454–457) plasmids into HL3T1 cells. Plasmids pSV2Tat and pAL express the first exon of Tat protein and luciferase enzyme, respectively. Luciferase reporter gene provides an internal control. Transfection of HeLa cells with pSV2Tat enhanced transcription, as determined by CAT activity. As shown in FIG. 5(*a*), increasing amounts of the tripeptide ID# 1 resulted in a decrease of CAT activity (left hand bar of each pair) while luciferase activity (right hand bar of each pair) was not affected. In the presence of 700 niM concentrations of tripeptide ID#1, more than 90% of Tat trans-activation was inhibited. To rule out the possibility that the observed inhibition of transactivation could be due to some nonspecific toxicity of the tripeptide ID# 1 or reduction of pSV2Tat plasmid uptake, transcription of the luciferase gene was monitored (FIG. 5(*a*)). Transcription of the luciferase gene was not affected by the presence of tripeptide ID#1. Cell viability assays showed that tripeptide ID# 1 treatment was not toxic to the cells (FIG. 5(*b*)). Further control experiments showed that weaker TAR RNA binding ligands, such as L-argininamide (FIG. 5(*a*), control columns) and a scrambled Tat peptide containing D-amino acids, had no inhibitory effect on Tat transactivation (Huq (1999) *Biochemistry* 38, 5172–5177). Thus, because tripeptide ID#1 binds TAR RNA and inhibits Tat-TAR interactions in vivo, tripeptide ID#1 is useful for treating or preventing HIV or AIDS in a patient.

The present invention is not to be limited in scope by the specific embodiments disclosed in the Examples, which are intended as illustrations of a few aspects of the invention. Any embodiments which are functionally equivalent are within the scope of this invention. Indeed, various modifications of the invention in addition to those shown and described herein will become apparent to those skilled in the art and are intended to fall within the appended claims.

All references disclosed herein are hereby incorporated by reference in their entirety.

What is claimed is:

1. A method for identifying a test compound that binds to a target RNA molecule, comprising the steps of:
   a. contacting an aqueous solution of a dye-labeled target RNA molecule with a plurality of test compounds attached to a plurality of solid supports, wherein each solid support has substantially one type of test compound attached to its surface under conditions that permit direct binding of the dye-labeled RNA to a solid-support attached test compound so that a selected a dye-labeled target RNA:support-attached test compound complex is formed;
   b. selecting the dye-labeled target RNA:support-attached test compound formed in step (a) from uncomplexed target RNA molecules and test compounds; and
   c. determining the structure of the test compound of the RNA:support-attached test compound complex selected in step (b) by decoding said solid support.

2. A method for identifying a test compound that binds to a target RNA molecule, comprising the step of determining the structure of a test compound of an RNA:support-attached test compound complex formed from contacting an aqueous solution of a dye-labeled target RNA molecule with a plurality of test compounds attached to a plurality of solid supports, wherein each solid support has substantially one type of test compound attached to its surface under conditions that permit direct binding of the dye-labeled RNA to a solid-support attached test compound so that a selected a dye-labeled target RNA:support-attached test compound complex is formed and wherein said dye-labeled target RNA:support-attached test compound is separated from uncomplexed target RNA molecules and test compounds, wherein said structure is determined by decoding said solid support.

3. The method of claim 1, wherein the aqueous solution comprises from about 2 mM to about 20 mM KCl, from about 1 mM to about 100 mM NaCl, and from about 0 mM to about 20 mM $MgCl_2$.

4. The method of claim 2, wherein the aqueous solution comprises from about 2 mM to about 20 mM KCl, from about 1 mM to about 100 mM NaCl, and from about 0 mM to about 20 mM $MgCl_2$.

5. The method of claim 1, wherein the aqueous solution comprises a buffer.

6. The method of claim 2, wherein the aqueous solution comprises a buffer.

7. The method of claim 1, wherein the aqueous solution comprises a detergent or surfactant.

8. The method of claim 2, wherein the aqueous solution comprises a detergent or surfactant.

9. The method of claim 1, wherein the aqueous solution comprises an unlabeled target RNA molecule having at least one mutation at the binding site of said test compound.

10. The method of claim 2, wherein the aqueous solution comprises an unlabeled target RNA molecule having at least one mutation at the binding site of said test compound.

11. The method of claim 1, wherein the dye of the dye-labeled target RNA molecule is selected from the group consisting of a fluorescent dye, a phosphorescent dye, an ultraviolet dye, an infrared dye, and a visible dye.

12. The method of claim 2, wherein the dye of the dye-labeled target RNA molecule is selected from the group consisting of a fluorescent dye, a phosphorescent dye, an ultraviolet dye, an infrared dye and a visible dye.

13. The method of claim 11, wherein said target RNA is labeled with a visible dye.

14. The method of claim 12, wherein said target RNA is labeled with a visible dye.

15. The method of claim 13, wherein the visible dye is disperse red.

16. The method of claim 14, wherein the visible dye is disperse red.

17. The method of claim 1, wherein said solid support is selected from the group consisting of a silica gel, a resin, a derivatized plastic film, a glass bead, cotton, a plastic bead, a polystyrene bead, an alumina gel, and a polysaccharide.

18. The method of claim 2, wherein said solid support is selected from the group consisting of a silica gel, a resin, a derivatized plastic film, a glass bead, cotton, a plastic bead, a polystyrene bead, an alumina gel, and a polysaccharide.

19. The method of claim 1, wherein determining the structure of substantially one type of test compound comprises using a direct technique selected from the group consisting of nucleic acid sequencing of the test compound, peptide sequencing of the test compound, NMR, Fourier transform infra-red spectroscopy, Fourier transform Raman spectroscopy, electrospray ionization mass spectrometry, matrix-assisted laser desorption/ionization mass spectrometry, HPLC, and X-ray photoelectron spectroscopy.

20. The method of claim 2, wherein determining the structure of substantially one type of test compound comprises using a direct technique selected from the group consisting of nucleic acid sequencing of the test compound, peptide sequencing of the test compound, NMR, Fourier transform infra-red spectroscopy, Fourier transform Raman spectroscopy, electrospray ionization mass spectrometry, matrix-assisted laser desorption/ionization mass spectrometry, HPLC, and X-ray photoelectron spectroscopy.

21. The method of claim 1, wherein determining the structure of substantially one type of test compound comprises using an indirect technique selected from the group consisting of nucleic acid sequencing of a molecular tag, peptide sequencing of a molecular tag, indexing using readable molecular tags, use of laser optical synthesis chips, and use of fluorescently labeled solid supports.

22. The method of claim 2, wherein determining the structure of substantially one type of test compound comprises using an indirect technique selected from the group consisting of nucleic acid sequencing of a molecular tag, peptide sequencing of a molecular tag, indexing using readable molecular tags, use of laser optical synthesis chips, and use of fluorescently labeled solid supports.

23. The method of claim 1, wherein the test compound is selected from the group consisting of peptides, peptide analogs, nucleic acids, nucleic acid analogs, PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose.

24. The method of claim 2, wherein the test compound is selected from the group consisting of peptides, peptide analogs, nucleic acids, nucleic acid analogs, hormones, antigens, synthetic or naturally occurring drugs, opiates, dopamine, PNAs, serotonin, catecholamines, thrombin, acetylcholine, prostaglandins, organic molecules, pheromones, adenosine, sucrose, glucose, lactose and galactose.

25. The method of claim 1, wherein the target RNA is selected from the group consisting of a mammalian RNA, a viral RNA, a bacterial RNA, a protozoal RNA, and a fungal RNA.

26. The method of claim 2, wherein the target RNA is selected from the group consisting of a mammalian RNA, a viral RNA, a bacterial RNA, a protozoal RNA, and a fungal RNA.

27. The method of claim 1, wherein the target RNA is selected from the group consisting of a messenger RNA, a transfer RNA, a ribosomal RNA and an enzymatic RNA.

28. The method of claim 2, wherein the target RNA is selected from the group consisting of a messenger RNA, a transfer RNA, a ribosomal RNA and an enzymatic RNA.

29. The method of claim 27, wherein said messenger RNA encodes a protein selected from the group consisting of amyloid protein, amyloid precursor protein, angiostatin, endostatin, METH-1, METH-2, Factor IX, Factor VIII, collagen, cyclin dependent kinase, cyclin D1, cyclin E, WAF 1, cdk4 inhibitor, MTS1, cystic fibrosis transmembrane conductance regulator gene, IL-1, IL-2, IL-3, IL-4, IL-5, IL-6, IL-7, IL-8, IL-9, IL-10, IL-11, IL-12, IL-13, IL-14, IL-15, IL-16, IL-17, erythropoietin, G-CSF, GM-CSF, M-CSF, SCF, thrombopoietin, BNDF, BMP, GGRP, EGF, FGF, GDNF, GGF, HGF, IGF-1, IGF-2, KGF, myotrophin, NGF, OSM, PDGF, somatotrophin, TGF-β, TGF-α, VEGF, interferon, TNF-α, TNF-β, cathepsin K, cytochrome p-450, farnesyl transferase, glutathione-s transferase, heparanase, HMG CoA synthetase, n-acetyltransferase, phenylalanine hydroxylase, phosphodiesterase, ras carboxyl-terminal protease, telomerase, TNF converting enzyme, E-cadherin, N-cadherin, selectin, CD40, 5-α reductase, atrial natriuretic factor, calcitonin, corticotrophin releasing factor, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, thyroid stimulating hormone, antibodies, CTLA4, hemagglutinin, MHC proteins, VLA-4, kallikrein-kininogen-kinin system, CD4, sis, hst, ras, abl, mos, myc, fos, jun, H-ras, ki-ras, c-fms, bcl-2, L-myc, c-myc, gip, gsp, HER-2, bombesin receptor, estrogen receptor, GABA receptor, EGFR, PDGFR, FGFR, NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors, tissue plasminogen activator; transmembrane receptors, calcium pump, proton pump, Na/Ca exchanger, MRP 1, MRP2, P170, LRP, cMOAT, transferrin, APC, brcal, brca2, DCC, MCC, MTS1, NF1, NF2, nm23, p53 and Rb.

30. The method of claim 28, wherein said target RNA is a messenger RNA that encodes a protein selected from the group consisting of amyloid protein, amyloid precursor protein, angiostatin, endostatin, METH-1, METH-2, Factor IX, Factor VIII, collagen, cyclin dependent kinase, cyclin D1, cyclin E, WAF 1, cdk4 inhibitor, MTS 1, cystic fibrosis transmembrane conductance regulator gene, IL-1, IL-2, IL-3, IL-4, IL-5, IL-6, IL-7, IL-8, IL-9, IL-10, IL-11, IL-12, IL-13, IL-14, IL-15, IL-16, IL-17, erythropoietin, G-CSF, GM-CSF, M-CSF, SCF, thrombopoietin, BNDF, BMP, GGRP, EGF, FGF, GDNF, GGF, HGF, IGF-1, IGF-2, KGF, myotrophin, NGF, OSM, PDGF, somatotrophin, TGF-β, TGF-α, VEGF, interferon, TNF-α, TNF-β, cathepsin K, cytochrome p-$^4$50, farnesyl transferase, glutathione-s transferase, heparanase, HMG CoA synthetase, n-acetyltransferase, phenylalanine hydroxylase, phosphodiesterase, ras carboxyl-terminal protease, telomerase, TNF converting enzyme, E-cadherin, N-cadherin, selectin, CD40, 5-α reductase, atrial natriuretic factor, calcitonin, corticotrophin releasing factor, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, thyroid stimulating hormone, antibodies, CTLA4, hemagglutinin, MHC proteins, VLA-4, kallikrein-kininogen-kinin system, CD4, sis, hst, ras, abl, mos, myc, fos, jun, H-ras, ki-ras, c-fms, bcl-2, L-myc, c-myc, gip, gsp, HER-2, bombesin receptor, estrogen receptor, GABA receptor, EGFR, PDGFR, FGFR, NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors, tissue plasminogen activator; transmembrane receptors, calcium pump, proton pump, Na/Ca exchanger, MRP 1, MRP2, P170, LRP, cMOAT, transferrin, APC, brcal, brca2, DCC, MCC, MTSI, NF1, NF2, nm23, p53 and Rb.

31. A method for forming a target RNA:test compound complex, comprising the step of contacting a target RNA molecule with the test compound identified from the method of claim 1.

32. The method of claim 31, wherein the contacting occurs in the presence of an aqueous solution.

33. The method of claim 32, wherein the aqueous solution comprises from about 2 mM to about 20 mM KCl, from about 1 mM to about 100 mM NaCl, and from about 0 mM to about 20 mM $MgCl_2$.

34. The method of claim 32, wherein the aqueous solution comprises a buffer.

35. The method of claim 32, wherein the aqueous solution comprises a detergent or surfactant.

36. The method of claim 31, wherein the step of contacting a target RNA with the test compound displaces a ligand of said target RNA.

37. The method of claim 31, wherein the step of contacting a target RNA with the test compound occurs in vivo.

38. A method for increasing or decreasing the production of a protein comprising the step of contacting a target messenger RNA molecule that encodes said protein with the test compound identified from the method of claim 1.

39. The method of claim 38, wherein the test compound is selected from the group consisting of peptides, peptide analogs, nucleic acids, nucleic acid analogs, hormones, antigens, synthetic or naturally occurring drugs, opiates, dopamine, PNAs, serotonin, catecholamines, thrombin, acetylcholine, prostaglandins, organic molecules, pheromones, adenosine, sucrose, glucose, lactose and galactose.

40. The method of claim 38, wherein the target RNA is selected from the group consisting of a mammalian RNA, a viral RNA, a bacterial RNA, a protozoal RNA, and a fungal RNA.

41. The method of claim 40, wherein the target RNA is selected from the group consisting of a messenger RNA, a transfer RNA, a ribosomal RNA and an enzymatic RNA.

42. The method of claim 41, wherein the messenger RNA encodes a protein selected from the group consisting of amyloid protein, amyloid precursor protein, angiostatin, endostatin, METH-1, METH-2, Factor IX, Factor VIII, collagen, cyclin dependent kinase, cyclin D1, cyclin E, WAF1, cdk4 inhibitor, MTS1, cystic fibrosis transmembrane conductance regulator gene, IL-1, IL-2, IL-3, IL-4, IL-5, IL-6, IL-7, IL-8, IL-9, IL-10, IL-11, IL-12, IL-13, IL-14, IL-15, IL-16, IL-17, erythropoietin, G-CSF, GM-CSF, M-CSF, SCF, thrombopoietin, BNDF, BMP, GGRP, EGF, FGF, GDNF, GGF, HGF, IGF-1, IGF-2, KGF, myotrophin, NGF, OSM, PDGF, somatotrophin, TGF-β, TGF-α, VEGF, interferon, TNF-α, TNF-β, cathepsin K, cytochrome p-450, farnesyl transferase, glutathione-s transferase, heparanase, HMG CoA synthetase, n-acetyltransferase, phenylalanine hydroxylase, phosphodiesterase, ras carboxyl-terminal protease, telomerase, TNF converting enzyme, E-cadherin, N-cadherin, selectin, CD40, 5-α reductase, atrial natriuretic factor, calcitonin, corticotrophin releasing factor, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, thyroid stimulating hormone, antibodies, CTLA4, hemagglutinin, MHC proteins, VLA-4, kallikrein-kininogen-kinin system, CD4, sis, hst, ras, abl, mos, myc, fos, jun, H-ras, ki-ras, c-fms, bcl-2, L-myc, c-myc, gip, gsp, HER-2, bombesin receptor, estrogen receptor, GABA receptor, EGFR, PDGFR, FGFR, NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors, tissue plasminogen activator; transmembrane receptors, calcium pump, proton pump, Na/Ca exchanger, MRP 1, MRP2, P170, LRP, cMOAT, transferrin, APC, brcal, brca2, DCC, MCC, MTS1, NF1, NF2, nm23, p53 and Rb.

43. The method of claim 38, wherein increasing or decreasing the production of a protein interferes with the progression of a disease associated with decreasing or increasing the production of said protein, respectively.

44. The method of claim 43, wherein the disease is selected from the group consisting of amyloidosis, hemophilia, Alzheimer's disease, atherosclerosis, cancer, giantism, dwarfism, hypothyroidism, hyperthyroidism, inflammation, cystic fibrosis, autoimmune disorders, diabetes, aging, obesity, neurodegenerative disorders, and Parkinson's disease.

45. The method of claim 43, wherein said disease is caused by a bacteria, a fungus, a protozoa, or a virus.

46. The method of claim 45, wherein the disease is selected from the group consisting of HIV infection, AIDS, human T-cell leukemia, SIV infection, FIV infection, feline leukemia, hepatitis A, hepatitis B, hepatitis C, Dengue fever, malaria, rotavirus infection, severe acute gastroenteritis, diarrhea, encephalitis, hemorrhagic fever, syphilis, legionella, whooping cough, gonorrhea, sepsis, influenza, pneumonia, tinea infection, candida infection, and meningitis.

47. The method of claim 23, wherein the test compound is selected from the group consisting of:

$H_2N$-(L)Lys-(D)Lys-(L)Asn-OH,
$H_2N$-(L)Lys-(D)Lys-(D)Asn-OH,
$H_2N$-(L)Lys-(L)Lys-(L)Asn-OH,
$H_2N$-(L)Arg-(D)Lys-(L)Asn-OH,
$H_2N$-(L)Arg-(D)Lys-(L)Val-OH,
$H_2N$-(L)Arg-(D)Lys-(L)Arg-OH,
$H_2N$-(D)Thr-(D)Lys-(L)Asn-OH, and
$H_2N$-(D)Thr-(D)Lys-(L)Phe-OH.

48. The method of claim 24, wherein the test compound is selected from the group consisting of:

$H_2N$-(L)Lys-(D)Lys-(L)Asn-OH,
$H_2N$-(L)Lys-(D)Lys-(D)Asn-OH,
$H_2N$-(L)Lys-(L)Lys-(L)Asn-OH,
$H_2N$-(L)Arg-(D)Lys-(L)Asn-OH,
$H_2N$-(L)Arg-(D)Lys-(L)Val-OH,
$H_2N$-(L)Arg-(D)Lys-(L)Arg-OH,
$H_2N$-(D)Thr-(D)Lys-(L)Asn-OH, and
$H_2N$-(D)Thr-(D)Lys-(L)Phe-OH.

49. The method of claim 27, wherein the target RNA is HIV TAR RNA.

50. The method of claim 28, wherein the target RNA is HIV TAR RNA.

* * * * *

SEQUENCE LISTING

<160> NUMBER OF SEQ ID NOS: 6

<210> SEQ ID NO 1
<211> LENGTH: 29
<212> TYPE: RNA
<213> ORGANISM: HIV-1

<400> SEQUENCE: 1
ggcagaucug agccugggag cucucugcc         29

<210> SEQ ID NO 2
<211> LENGTH: 10
<212> TYPE: PRT
<213> ORGANISM: HIV-1

<400> SEQUENCE: 2

Gly Arg Lys Lys Arg Arg Gln Arg Arg Arg
 1               5                  10

<210> SEQ ID NO 3
<211> LENGTH: 47
<212> TYPE: DNA
<213> ORGANISM: Artificial Sequence
<220> FEATURE:
<223> OTHER INFORMATION: Template strand

<400> SEQUENCE: 3
ggcagagagc tcccaggctc agatctgccc tatagtgaat cgtatta         47

<210> SEQ ID NO 4
<211> LENGTH: 44
<212> TYPE: DNA
<213> ORGANISM: Artificial Sequence
<220> FEATURE:
<223> OTHER INFORMATION: Template strand

<400> SEQUENCE: 4
ggcagagagc tcccaggctc tctgccctat agtgaatcgt atta         44

```
<210> SEQ ID NO 5
<211> LENGTH: 26
<212> TYPE: RNA
<213> ORGANISM: Artificial Sequence
<220> FEATURE:
<223> OTHER INFORMATION: Bulge mutant TAR

<400> SEQUENCE: 5
ggcagagagc cugggagcuc ucugcc                                              26

<210> SEQ ID NO 6
<211> LENGTH: 18
<212> TYPE: DNA
<213> ORGANISM: Artificial Sequence
<220> FEATURE:
<223> OTHER INFORMATION: T7 promoter

<400> SEQUENCE: 6
taatacgact cactatag                                                       18
```